United States Patent
Wang et al.

(10) Patent No.: US 10,899,763 B2
(45) Date of Patent: Jan. 26, 2021

(54) CRYSTALLINE FORMS OF SALTS OF FUSED PENTA-CYCLIC DIHYDRODIAZEPINOCARBAZOLONES, AND USES THEREOF

(71) Applicant: BEIGENE, LTD., Grand Cayman (KY)

(72) Inventors: Hexiang Wang, Beijing (CN);
Xianzhao Kuang, Beijing (CN);
Changyou Zhou, Princeton, NJ (US)

(73) Assignee: BEIGENE, LTD., Grand Cayman (KY)

( * ) Notice: Subject to any disclaimer, the term of this patent is extended or adjusted under 35 U.S.C. 154(b) by 0 days.

(21) Appl. No.: 16/488,085

(22) PCT Filed: Feb. 27, 2018

(86) PCT No.: PCT/CN2018/077433
§ 371 (c)(1),
(2) Date: Aug. 22, 2019

(87) PCT Pub. No.: WO2018/157794
PCT Pub. Date: Sep. 7, 2018

(65) Prior Publication Data
US 2020/0157103 A1  May 21, 2020

(30) Foreign Application Priority Data
Feb. 28, 2017 (CN) .................. PCT/CN2017/075139

(51) Int. Cl.
C07D 487/22 (2006.01)
A61K 31/55 (2006.01)
A61P 35/00 (2006.01)
C07D 471/22 (2006.01)

(52) U.S. Cl.
CPC ............ C07D 471/22 (2013.01); A61P 35/00 (2018.01); C07B 2200/13 (2013.01)

(58) Field of Classification Search
CPC ........ C07D 487/22; A61K 31/55; A61P 35/00
See application file for complete search history.

(56) References Cited

U.S. PATENT DOCUMENTS

| 9,260,440 B2 | 2/2016 | Zhou et al. |
| 9,617,273 B2 | 4/2017 | Zhou et al. |
| 10,112,952 B2 | 10/2018 | Zhou et al. |
| 10,457,680 B2 | 10/2019 | Wang et al. |
| 10,501,467 B2 | 12/2019 | Zhou et al. |
| 2008/0146638 A1 | 6/2008 | Giranda et al. |
| 2015/0175617 A1 | 6/2015 | Zhou et al. |
| 2016/0159811 A1 | 6/2016 | Zhou et al. |
| 2016/0222012 A1 | 8/2016 | Ruan |
| 2017/0305921 A1 | 10/2017 | Zhou et al. |
| 2019/0016731 A1 | 1/2019 | Zhou et al. |
| 2019/0177325 A1 | 6/2019 | Wang et al. |
| 2020/0030339 A1 | 1/2020 | Wang et al. |
| 2020/0155567 A1 | 5/2020 | Wang et al. |

FOREIGN PATENT DOCUMENTS

| CN | 103703004 A | 4/2014 |
| CN | 106220635 A | 12/2016 |
| JP | 2002-534523 | 10/2002 |
| WO | WO 2000/042040 | 7/2000 |
| WO | WO 2002/044183 | 6/2002 |
| WO | WO 2004/063198 | 7/2004 |
| WO | WO 2010/017055 | 2/2010 |
| WO | WO 2013/097225 | 7/2013 |
| WO | WO 2015/035606 | 3/2015 |
| WO | WO 2016/000619 | 1/2016 |
| WO | WO 2017/032289 | 3/2017 |
| WO | WO 2018/059437 | 4/2018 |
| WO | WO 2018/157794 | 9/2018 |
| WO | WO 2019/015561 | 1/2019 |

OTHER PUBLICATIONS

Supplementary European Search Report for European Application No. 11878508.8, dated Sep. 22, 2015, 3 pages.
International Preliminary Report on Patentability for International Application No. PCT/CN2011/085148, dated Jul. 1, 2014, 7 pages.
International Search Report and Written Opinion for International Application No. PCT/CN2011/085148, dated Sep. 27, 2012, 12 pages.
Extended European Search Report for European Application No. 16838548.2, dated Dec. 19, 2018, 8 pages.
International Search Report and Written Opinion for International Application No. PCT/CN2016/096200, dated Nov. 11, 2016, 12 pages.
International Search Report and Written Opinion for International Application No. PCT/CN2017/103660, dated Jan. 9, 2018, 11 pages.
International Search Report and Written Opinion for International Application No. PCT/CN2018/077433, dated Jun. 5, 2018, 11 pages.
International Search Report and Written Opinion for International Application No. PCT/CN2018/095911, dated Oct. 26, 2018, 9 pages.
Chen, A., "PARP inhibitors: its role in treatment of cancer," Chinese Journal of Cancer, 2011, vol. 30, Issue 7, pp. 463-471.
Morissette, S. L., "High-throughput crystallization: polymorphs, salts, co-crystals and solvates of pharmaceutical solids," Advanced Drug Delivery Reviews, vol. 56, No. 3, Feb. 2004, pp. 275-300.
Fujiwara, M. et al., "First-principles and direct design approaches for the control of pharmaceutical crystallization," Journal of Process Control, vol. 15, No. 5, Aug. 2005, pp. 493-504.
Variankaval, N. et al., "From form to function: Crystallization of active pharmaceutical ingredients," AIChE Journal, vol. 54, No. 7, Jul. 2008, pp. 1682-1688.

(Continued)

Primary Examiner — Bruck Kifle
(74) Attorney, Agent, or Firm — Cooley LLP

(57) ABSTRACT

Disclosed herein are salts of (R)-2-fluoro-10a-methyl-7,8,9,10,10a,11-hexahydro-5,6,7a,11-tetraazacyclohepta[def]cyclopenta[a]fluoren-4(5H)-one, and crystalline forms (polymorphs) thereof. Also disclosed herein are methods of preparing those crystalline forms, and methods of using at least one of those crystalline forms in treating a cancer responsive to inhibition of PARP, especially a cancer associated with BRCA1/2 mutant activities or other HR deficiencies, in a subject.

26 Claims, 13 Drawing Sheets

(56) References Cited

OTHER PUBLICATIONS

Caira, M. R., "Crystalline polymorphism of organic compounds," Topics in Current Chemistry, vol. 198, 1998, pp. 163-208.
Underhill, C. et al., "A review of PARP inhibitors: from bench to bedside," Annals of Oncology, Advance Access published Jul. 19, 2010, doi:10.1093/annonc/mdq322, Retrieved from the Internet: <URL: http://annonc.oxfordjournals.org/>, Retrieved from the Internet on Jun. 14, 2016, 12 pages.
STN International, RN: 1858211-28-5, STN Registry, Feb. 2, 2016, 2 pages.
Extended European Search Report for European Application No. 17183473.2, dated Apr. 4, 2018, 6 pages.
Extended European Search Report for European Application No. 17854887.1, dated May 25, 2020, 9 pages.
Higuchi, T. et al., "CTLA-4 Blockade Synergizes Therapeutically with PARP Inhibition in BRCA1-Deficient Ovarian Cancer," Cancer Immunol. Res., Nov. 2015, 3(11):1257-1268 (Author Manuscript).
Tang, Z. et al., "Abstract 1653: BGB-290: A highly potent and specific PARP½ inhibitor potentiates anti-tumor activity of chemotherapeutics in patient biopsy derived SCLC models," In: Proceedings of the 106th Annual Meeting of the American Association of Cancer Research; Apr. 18-22, 2015; Philadelphia, PA: AACR; Cancer Res. 2015;75(15 Suppl.); Abstract No. 1653, 5 pages.
U.S. National Library of Medicine, "History of Changes for Study: NCT02660034. The Safety, Pharmacokinetics and Antitumor Activity of the BGB-A317 in Combination With the BGB-290 in Subject With Tumors", ClinicalTrials.gov archive [Online], Aug. 27, 2016, Retrieved from the Internet: <URL: https://clinicaltrials.gov/ct2/history/NCT02660034?V_3=View#StudyPageTop>, Retrieved on Jun. 5, 2020, 4 pages.

CRYSTALLINE FORMS OF SALTS OF FUSED PENTA-CYCLIC DIHYDRODIAZEPINOCARBAZOLONES, AND USES THEREOF

CROSS-REFERENCE TO RELATED APPLICATIONS

This application is a U.S. National Stage Application under 35 U.S.C. § 371 of International Application No. PCT/CN2018/077433, filed Feb. 27, 2018, which claims the benefit of International Patent Application No. PCT/CN2017/075139, filed Feb. 28, 2017, the disclosures of which are hereby incorporated by reference in their entireties for all purposes.

FIELD OF THE INVENTION

Disclosed herein are salts of (R)-2-fluoro-10a-methyl-7,8,9,10,10a,11-hexahydro-5,6,7a,11-tetraazacyclohepta[def]cyclopenta[a]fluoren-4(5H)-one, and crystalline forms (polymorphs) thereof. Also disclosed herein are methods of preparing those crystalline forms, and methods of using at least one of those crystalline forms in treating a cancer responsive to inhibition of PARP, especially a cancer associated with BRCA1/2 mutant activities or other HR deficiencies, in a subject.

BACKGROUND OF THE INVENTION

One of the hallmarks and driving forces of cancer is genetic instability [Hanahan D and Weinberg R A, *Hallmarks of cancer: the next generation. Cell,* 2011. 144(5): p. 646-74.]. Specifically in familial cancers, mutations in the breast cancer susceptibility BRCA1 and BRCA2 tumor suppressor genes, key players in homologous recombination (HR), have been associated with an increased risk of developing breast or ovarian cancer [Li X and Heyer W D, *Homologous recombination in DNA repair and DNA damage tolerance. Cell Res,* 2008. 18(1): p. 99-113.]. It is in this patient population that inhibitors of poly (ADP-ribose) polymerase (PARP) have gained recent attention. PARP family members PARP1 and PARP2 play important roles in DNA replication, transcriptional regulation, and DNA damage repair [Rouleau M, Patel A, Hendzel M J, et al., *PARP inhibition: PARP1 and beyond. Nat Rev Cancer,* 2010. 10(4): p. 293-301.]. In 2005, two breakthrough Nature papers showed that PARP inhibitors given alone could kill cancer cells with pre-existing DNA repair defects, specifically mutations in BRCA1/2 genes [Bryant H E, Schultz N, Thomas H D, et al., *Specific killing of BRCA2-deficient tumours with inhibitors of poly(ADP-ribose) polymerase. Nature,* 2005. 434(7035): p. 913-7; Farmer H, McCabe N, Lord C J, et al., *Targeting the DNA repair defect in BRCA mutant cells as a therapeutic strategy. Nature,* 2005. 434 (7035): p. 917-21].

PARP inhibition and mutant BRCA were synthetically lethal in preclinical models, suggesting an elegant, targeted and minimally toxic way to treat patients.

(R)-2-fluoro-10a-methyl-7,8,9,10,10a,11-hexahydro-5,6,7a,11-tetraazacyclohepta[def]cyclopenta-[a]fluoren-4(5H)-one (hereafter Compound 1), has been disclosed as a highly selective and potent Parp1/2 inhibitor, See WO 2013/097225 A1, which is incorporated herein by reference.

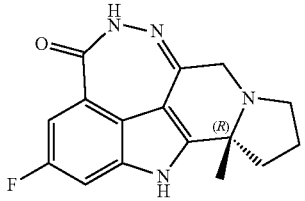

Compound 1

Compound 1 potently inhibits intracellular PARP activity and specifically inhibits the proliferation of cell lines with BRCA1/2 mutations or other HR deficiencies. It significantly induces tumor regression in BRCA1 mutation breast cancer xenograft model at much lower dose than olaparib. It has excellent DMPK properties and significant brain penetration.

Data generated in preclinical biochemical, cell-based and animal studies suggest that Compound 1 could offer significant patient benefit in inhibiting tumors harboring BRCA gene mutations or homologous recombination defects. It has good brain penetration and might show activity in more indication such as glioblastoma. In addition, food effect is a risk associated with administering a drug substance to a patient who has eaten recently. The risk derives from the potential that absorption into the bloodstream may be adversely affected to the point that the patient risks insufficient absorption to remedy the condition for which the drug was administered. However, there is still a need of a certain form of Compound 1 as the active pharmaceutical ingredient (API), which is physically and chemically stable, and easy to handle, and exhibits various release requirement properties to meet clinical requirements.

SUMMARY OF THE INVENTION

The inventors of the present application obtained salts of Compound 1 from the reaction of Crystalline sesqui-hydrate of Compound 1 as the starting material with some acids, and found that some of the obtained salts are crystalline, and exhibit particular dissolution profiles to meet various release requirements. The inventors found that one crystalline form of maleate salt of Compound 1 exhibits comparable solubility in FaSSIF (~0.2 mg/mL) and FeSSIF (~0.5 mg/mL) compared with that of Crystalline sesqui-hydrate of Compound 1 (<0.1 mg/mL and 1 mg/mL, respectively), suggesting that the crystalline maleate salt may be used to significantly reduce food effect. In addition, the crystalline maleate salt also exhibits steady dissolution profiles in bio-relevant media, suggesting an extended release profile in drug formulation. In addition, the inventors also found that one crystalline form of phosphate salt of Compound 1 and one crystalline form of fumarate salt of Compound 1 also exhibit particular dissolution profiles in bio-relevant media, i.e., they are found to exhibit higher solubility at the first time point, but the values went down after equilibrated for a longer time.

Disclosed herein are crystalline forms of salts of (R)-2-fluoro-10a-methyl-7,8,9,10,10a,11-hexahydro-5,6,7a,11-tetraazacyclohepta[def]cyclopenta-[a]fluoren-4(5H)-one (Compound 1), in particularly, phosphate, maleate and fumarate thereof. Also disclosed herein are methods of preparing those crystalline forms, a pharmaceutical composition comprising the same, and the method of using the same in treating a cancer responsive to inhibition of PARP.

In a first aspect, disclosed herein is a crystalline form of a salt of Compound 1, which has Formula I, Formula I wherein M is H$_3$PO$_4$ or maleic acid or fumaric acid, and m is a number of from about 0.5 to about 2.0.

In one embodiment of the first aspect, disclosed herein is a crystalline form of Compound 1 Phosphate. In some embodiments, the crystalline form of Compound 1 phosphate is a crystalline mono-hydrate (i.e., Crystalline Form of Compound 1 Phosphate, hereinafter Form A).

In another embodiment of the first aspect, disclosed herein is a crystalline form of Compound 1 maleate. In some embodiments, the crystalline form of Compound 1 maleate is an anhydrous non-solvated crystalline form (i.e., Crystalline Form of Compound 1 Maleate, hereinafter Form B).

In yet another embodiment of the first aspect, disclosed herein is crystalline form of Compound 1 fumarate. In some embodiments, the crystalline form of Compound 1 fumarate is a crystalline sesqui-hydrate (i.e., Crystalline Form of Compound 1 Fumarate, hereinafter Form C2).

In a second aspect, disclosed herein is methods of preparing the crystalline forms disclosed herein.

In a third aspect, disclosed herein is a pharmaceutical composition comprising a therapeutically effective amount of the crystalline form of a salt of Compound 1 disclosed herein. In some embodiments, the crystalline form is Form A, Form B, or Form C2.

In a fourth aspect, disclosed herein is a method of treating a disease, a disorder, or a condition associated with BRCA1/2 mutant activities or other HR deficiencies in a subject by administering to the subject the crystalline form of a salt of Compound 1 disclosed herein. In some embodiments, the crystalline form is Form A, Form B, or Form C2. In one embodiment, the disease or disorder or condition is a cancer selected from the group consisting of brain cancer, lung cancer including small cell lung cancer, kidney cancer, bone cancer, liver cancer, bladder cancer, breast, head and neck cancer, ovarian cancer, melanoma, skin cancer, adrenal cancer, cervical cancer, lymphoma, or thyroid tumors and their complications.

In a fifth aspect, disclosed herein is a use of the crystalline form of a salt of Compound 1 disclosed herein in manufacture of a medicament for treating a disease, a disorder, or a condition associated with BRCA1/2 mutant activities or other HR deficiencies. In some embodiments, the crystalline form is Form A, Form B, or Form C2. In one embodiment, the disease or disorder or condition is a cancer selected from the group consisting of brain cancer, lung cancer including small cell lung cancer, kidney cancer, bone cancer, liver cancer, bladder cancer, breast, head and neck cancer, ovarian cancer, melanoma, skin cancer, adrenal cancer, cervical cancer, lymphoma, or thyroid tumors and their complications.

DETAILED DESCRIPTION OF THE INVENTION

Definitions

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise. For example, a reference to "a crystalline form" includes one or more of such different crystalline forms and a reference to "the method" includes reference to equivalent steps and methods know to those of ordinary skill in the art that could be modified or substituted for the methods described herein.

As disclosed herein, the crystalline form is an approximately pure crystalline. The term "approximately pure" as herein used refers to at least 85 wt %, preferably at least 95 wt %, more preferably at least 99 wt % of the crystalline form at issue.

For crystalline forms disclosed herein, only the main peaks (i.e, the most characteristic, significant, unique and/or reproducible peaks) are summarized; additional peaks may be obtained from the diffraction spectra by conventional methods. The main peaks disclosed herein can be reproduced within the margin of error (±2 at the last given decimal place, or ±0.2 at the stated value).

Figure 2A:
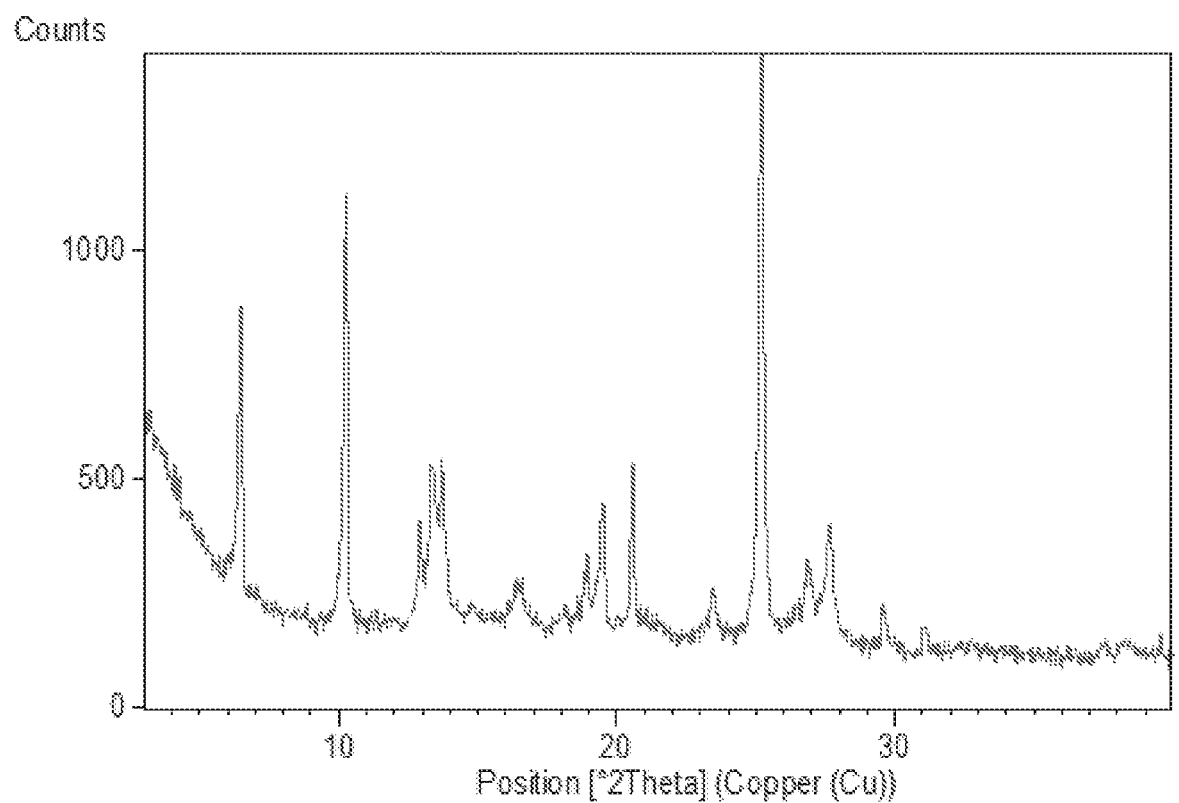
FIG. 2A shows the XRPD pattern of Form A.

As disclosed herein, a reference to an expression such as "an X-ray powder diffraction pattern substantially in accordance with FIG. 2A" refers to the X-ray powder diffraction pattern that show major peaks as in FIG. 2A, wherein major peaks refer to those with the relative intensity greater than 10%, preferably greater than 20%, relative to the highest peak (with its relative intensity designated to be 100%) in FIG. 2A.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

The term "therapeutically effective amount" as herein used, refers to the amount of a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

The pharmaceutical composition comprising the compound disclosed herein can be administered via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc, a filler such as starch, sucrose, etc a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

As disclosed herein, a "subject" refers to a human or a non-human animal.

The following techniques are used to identify, characterize or analyze a crystalline form: X-ray powder diffraction (XRPD) pattern, TGA and DSC, nuclear magnetic resonance (NMR), Chromatographic technique such as HPLC, and Ion chromatography (IC) method.

The X-ray powder diffraction (XRPD) patterns shown as in FIGS. 1A, 2A, 2C, 3A, 3D, 4A, 5A, 6C and 6D were generated on a PANalytical Empyrean X-ray powder diffractometer. The XRPD parameters used are listed in Table 1.

TABLE 1

Parameters for XPRD test

| Parameters | XRPD (Reflection Mode) |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0130 |
| Scan speed (°/min) | About 7 |

The differential scanning calorimetry (DSC) shown as in FIGS. 1B, 2B, 2D, 3B, 3E, 4B, 5B and 6A were generated on a TA Q200/Q2000 DSC from TA Instruments. The thermogravimetric analysis (TGA) shown as in FIGS. 1B, 2B, 2D, 3B, 3E, 4B, 5B and 6A were generated on a TA Q500/Q5000 TGA from TA Instruments. Detailed parameters of DSC and TGA used are listed in Table 2.

TABLE 2

Parameters for TGA and DSC test

| Parameters | TGA | DSC |
|---|---|---|
| Method | Ramp | Ramp |
| Sample pan | Aluminum, open | Aluminum, crimped |
| Temperature | RT - desired temperature | 25° C. - desired temperature |
| Heating rate | 10° C./min | 10° C./min |
| Purge gas | $N_2$ | $N_2$ |

The nuclear magnetic resonance (NMR) shown as in FIGS. 1C, 3C, 4C, 5C and 6B were collected on Bruker 400M NMR Spectrometer using DMSO-$d_6$.

Agilent 1100 HPLC was utilized and detailed chromatographic conditions for stoichiometry ratio measurement are listed in Table 3.

TABLE 3

Chromatographic conditions and parameters

| Parameters | Purity | Solubility |
|---|---|---|
| Column | Agilent C18, 150 × 4.6 mm, 3.5 μm | Waters Xbridge C18, 150 × 4.6 mm, 5 μm |

TABLE 3-continued

| Chromatographic conditions and parameters | | | | |
|---|---|---|---|---|
| Mobile phase | A: 0.1% TFA in H$_2$O<br>B: 0.1% TFA in acetonitrile | | | |
| | Time (min) | % B | Time (min) | % B |
| Gradient table | 0.0 | 10 | 0.0 | 10 |
| | 15.0 | 30 | 5.0 | 80 |
| | 20.0 | 90 | 6.0 | 80 |
| | 22.0 | 90 | 6.1 | 10 |
| | 22.1 | 10 | 8.0 | 10 |
| | 25.0 | 10 | — | — |
| Run time | 25.0 min | | 8.0 min | |
| Post time | 0.0 min | | 0.0 min | |
| Flow rate | 1.0 mL/min | | 1.0 mL/min | |
| Injection volume | 5 μL | | 5 μL | |
| Detector wavelength | UV at 225 nm,<br>reference 500 nm | | UV at 225 nm,<br>reference 500 nm | |
| Column temperature | 40° C. | | 40° C. | |
| Sampler temperature | RT | | RT | |
| Diluent | ACN + H$_2$O | | ACN | |

Ion chromatography (IC) method for counter-ion content measurement to determine stoichiometric ratio was listed in Table 4.

TABLE 4

| IC method for Cl$^-$, SO$_4^{2-}$ and PO$_4^{3-}$ content measurement | |
|---|---|
| Parameters | IC |
| Column | IonPac AS18 Analytical<br>Column (4 × 250 mm) |
| Mobile Phase | 25 mM NaOH |
| Injection volume | 25 μL |
| Flow rate | 1.0 mL/min |
| Cell temperature | 35° C. |
| Column temperature | 35° C. |
| Current | 80 mA |
| Run Time | 6.0 min (Cl$^-$), 12 min<br>(SO$_4^{2-}$) 28.0 min (PO$_4^{3-}$) |

In a first aspect, disclosed herein is a crystalline form of a salt of Compound 1, which has Formula I,

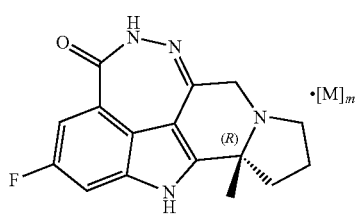

Formula I wherein M is H$_3$PO$_4$ or maleic acid or fumaric acid, and m is a number of from about 0.5 to about 2.0. In some embodiments, m is a number of from about 0.8 to about 1.2; preferably a number of from about 0.9 to about 1.1; more preferably a number of about 1.0.

Crystalline Form of Compound 1 Phosphate (Form A)

In one embodiment of the first aspect, disclosed herein is a crystalline form of phosphate salt of Compound 1 (Form A),

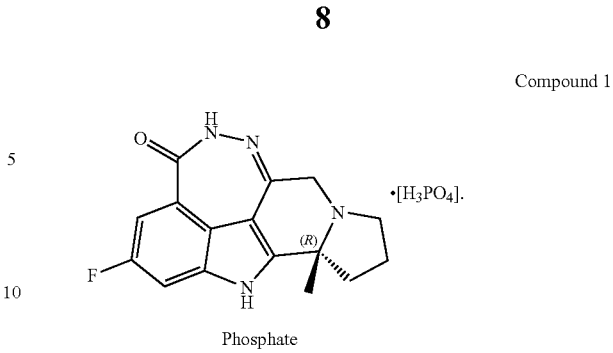

Compound 1

Phosphate

In some embodiments, the crystalline form of Compound 1 phosphate is approximately pure.

In some embodiments, Form A is a crystalline monohydrate.

In some embodiments, Form A is characterized by an X-ray powder diffraction pattern comprising diffraction peaks having 2θ angle values independently selected from: approximately 6.5±0.2°, 10.2±0.2°, and 25.2±0.2°.

In some embodiments, Form A is characterized by an X-ray powder diffraction pattern comprising diffraction peaks having 2θ angle values independently selected from: approximately 6.5±0.2°, 10.2±0.2°, 13.7±0.2°, 20.6±0.2°, and 25.2±0.2°.

In some embodiments, Form A is characterized by an X-ray powder diffraction pattern comprising diffraction peaks having 2θ angle values independently selected from: approximately 6.5±0.2°, 10.2±0.2°, 13.4±0.2°, 13.7±0.2°, 19.5±0.2°, 20.6±0.2°, 25.2±0.2°, and 27.6±0.2°.

In some embodiments, Form A is characterized by an X-ray powder diffraction pattern comprising diffraction peaks having 2θ angle values independently selected from: approximately 6.5±0.2°, 10.2±0.2°, 12.9±0.2°, 13.4±0.2°, 13.7±0.2°, 18.9±0.2°, 19.5±0.2°, 20.6±0.2°, 25.2±0.2°, 26.9±0.2°, and 27.6±0.2°.

In some embodiments, Form A has an X-ray powder diffraction pattern summarized in Table 5.

TABLE 5

| X-ray Diffraction Pattern of Form A | | | |
|---|---|---|---|
| Peak# | Diffraction angle<br>(2 theta) [°] | d-spacing<br>[Å] | Relative<br>intensity [%] |
| 1 | 6.463399 | 13.67543 | 46.55 |
| 2 | 10.248760 | 8.63137 | 72.01 |
| 3 | 12.923950 | 6.85010 | 17.24 |
| 4 | 13.370280 | 6.62242 | 27.51 |
| 5 | 13.714450 | 6.45699 | 28.91 |
| 6 | 16.454250 | 5.38750 | 8.20 |
| 7 | 18.910310 | 4.69295 | 11.78 |
| 8 | 19.489270 | 4.55483 | 22.68 |
| 9 | 20.575020 | 4.31685 | 29.86 |
| 10 | 23.463790 | 3.79151 | 8.98 |
| 11 | 25.203980 | 3.53354 | 100.00 |
| 12 | 26.896170 | 3.31494 | 13.61 |
| 13 | 27.650430 | 3.22621 | 20.47 |
| 14 | 29.605660 | 3.01744 | 6.79 |
| 15 | 31.073710 | 2.87815 | 4.03 |

In some embodiments, Form A has an X-ray powder diffraction pattern substantially in accordance with FIG. 2A.

Figure 2B:
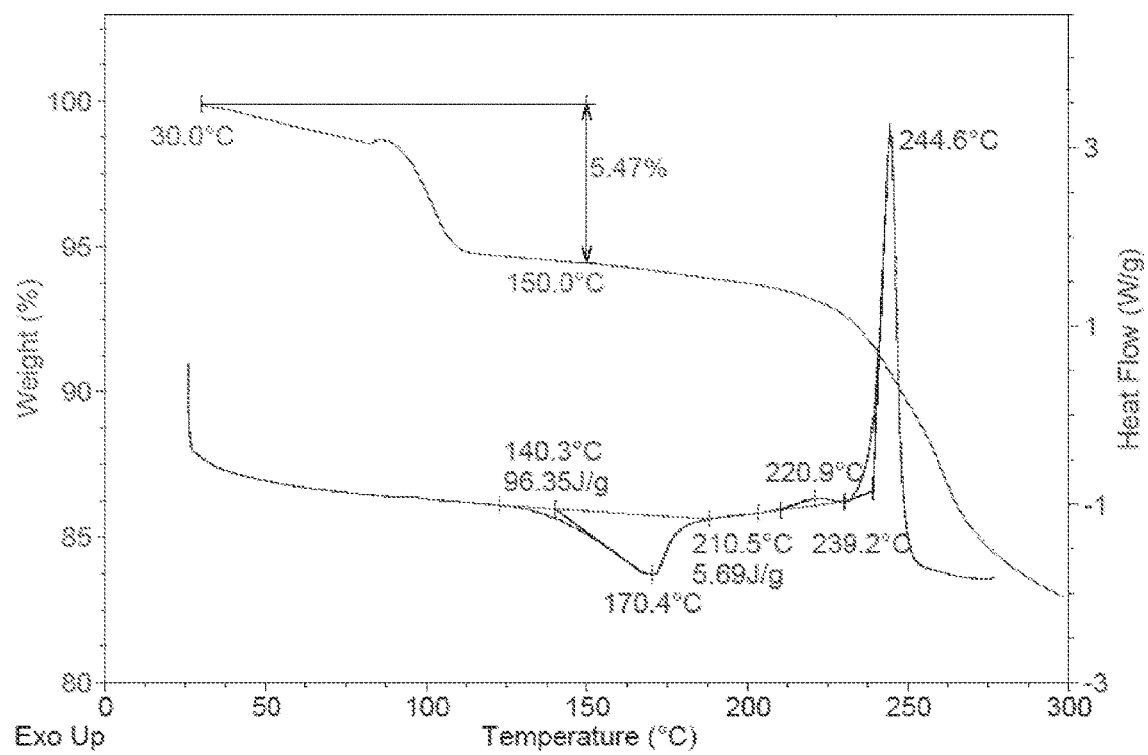
FIG. 2B shows the TGA/DSC curve of Form A.
Figure 2C:
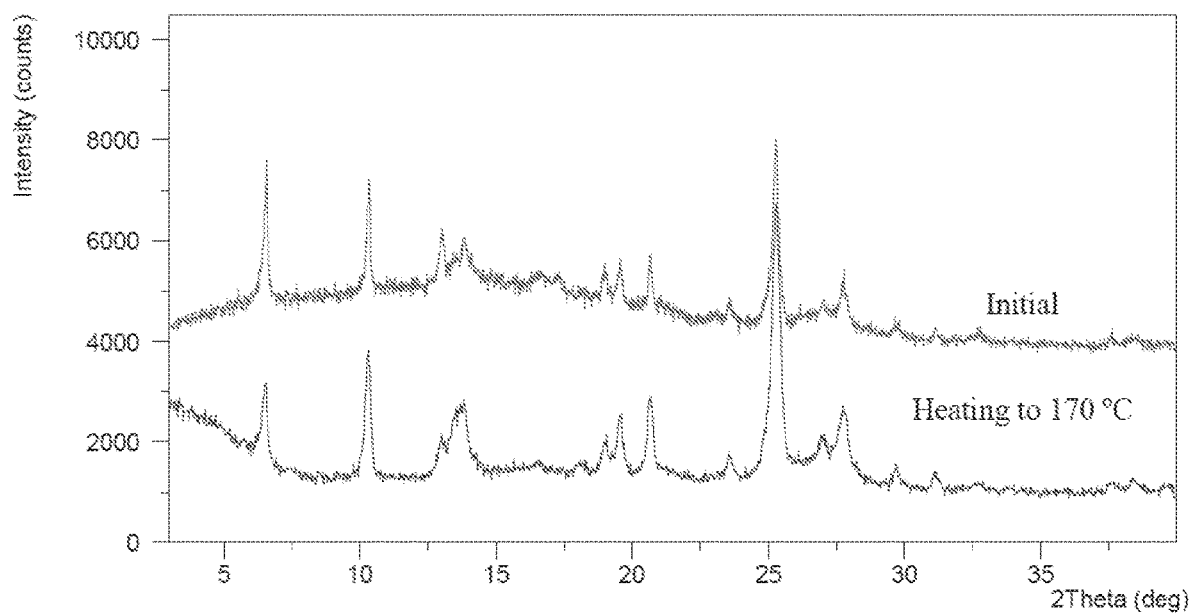
FIG. 2C shows the XRPD patterns overlay of Form A before and after heating (170° C.).

Preferably, Form A has a DSC substantially in accordance with FIG. 2B, and/or a TGA substantially in accordance with FIG. 2B.

Crystalline Form of Compound 1 Maleate (Form B)

In another embodiment of the first aspect, disclosed herein is a crystalline form of maleate salt of Compound 1 (Form B),

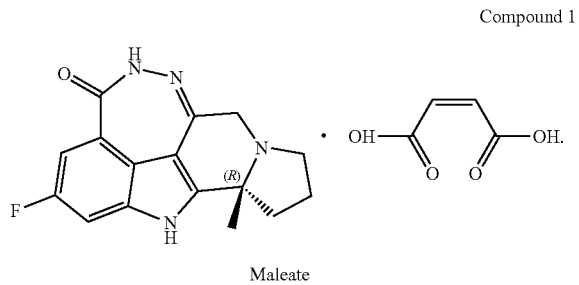

Compound 1 Maleate

In some embodiments, the crystalline form of Compound 1 Maleate is approximately pure.

In some embodiments, Form B is an anhydrous non-solvated crystalline form.

In some embodiments, Form B is characterized by an X-ray powder diffraction pattern comprising diffraction peaks having 2θ angle values independently selected from: approximately 6.3±0.2°, 10.0±0.2°, 14.1±0.2°, and 25.0±0.2°.

In some embodiments, Form B is characterized by an X-ray powder diffraction pattern comprising diffraction peaks having 2θ angle values independently selected from: approximately 6.3±0.2°, 10.0±0.2°, 14.1±0.2°, 17.8±0.2°, 19.2±0.2°, and 25.0±0.2°.

In some embodiments, Form B is characterized by an X-ray powder diffraction pattern comprising diffraction peaks having 2θ angle values independently selected from: approximately 6.3±0.2°, 10.0±0.2°, 12.8±0.2°, 14.1±0.2°, 17.3±0.2°, 17.8±0.2°, 19.2±0.2°, 19.5±0.2°, 25.0±0.2°, 26.1±0.2°, and 28.2±0.2°.

In some embodiments, Form B is characterized by an X-ray powder diffraction pattern comprising diffraction peaks having 2θ angle values independently selected from: approximately 6.3±0.2°, 10.0±0.2°, 12.8±0.2°, 14.1±0.2°, 17.3±0.2°, 17.8±0.2°, 19.2±0.2°, 19.5±0.2°, 25.0±0.2°, 26.1±0.2°, 28.2±0.2°, and 29.3±0.2°.

In some embodiments, Form B has an X-ray powder diffraction pattern summarized in Table 6.

TABLE 6

X-ray Diffraction Pattern of Form B

| Peak# | Diffraction angle (2 theta) [°] | d-spacing [Å] | Relative intensity [%] |
|---|---|---|---|
| 1 | 6.272459 | 14.09128 | 74.61 |
| 2 | 9.977965 | 8.86500 | 86.40 |
| 3 | 12.764850 | 6.93512 | 13.86 |
| 4 | 14.105030 | 6.27906 | 88.04 |
| 5 | 17.277720 | 5.13253 | 18.74 |
| 6 | 17.830720 | 4.97458 | 22.01 |
| 7 | 19.217330 | 4.61866 | 27.13 |
| 8 | 19.531110 | 4.54516 | 13.98 |
| 9 | 22.698480 | 3.91759 | 2.40 |
| 10 | 25.009750 | 3.56054 | 100.00 |
| 11 | 26.153560 | 3.40736 | 14.31 |
| 12 | 28.213100 | 3.16313 | 18.27 |
| 13 | 29.378220 | 3.04028 | 11.36 |
| 14 | 32.418420 | 2.76178 | 2.51 |
| 15 | 35.597280 | 2.52210 | 5.74 |

Figure 3A:
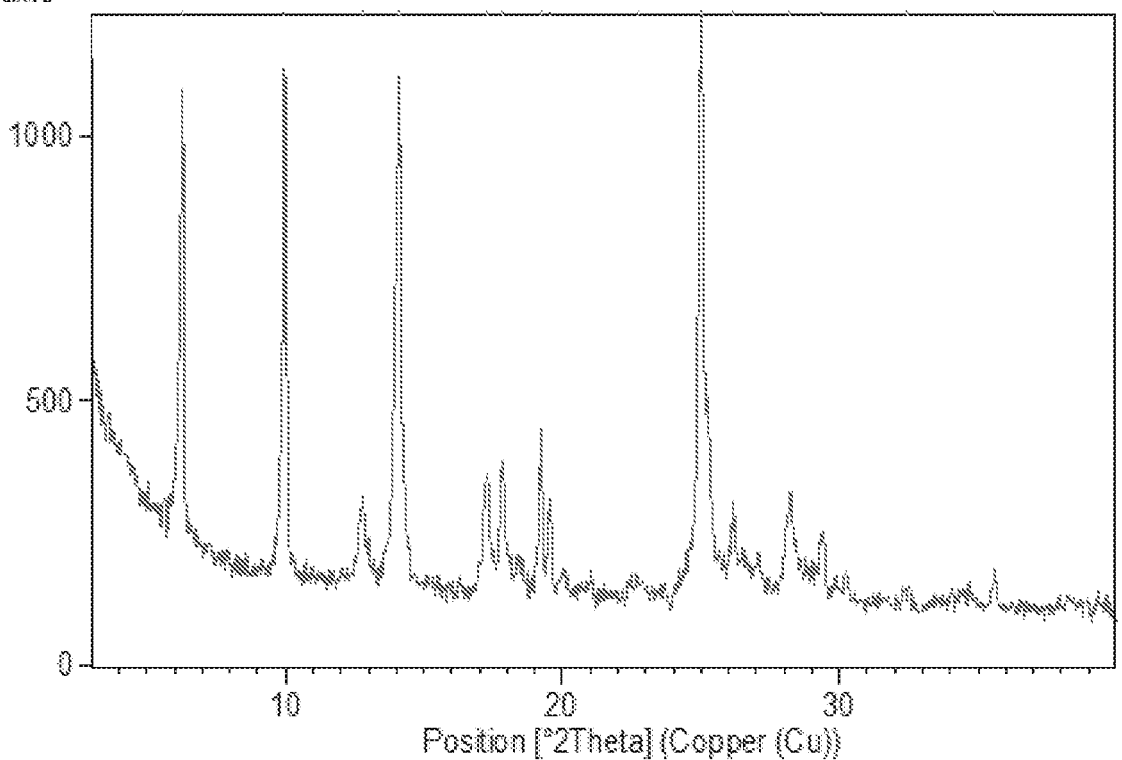
FIG. 3A shows the XRPD pattern of Form B.

In some embodiments, Form B has an X-ray powder diffraction pattern substantially in accordance with FIG. 3A.

Figure 3B:
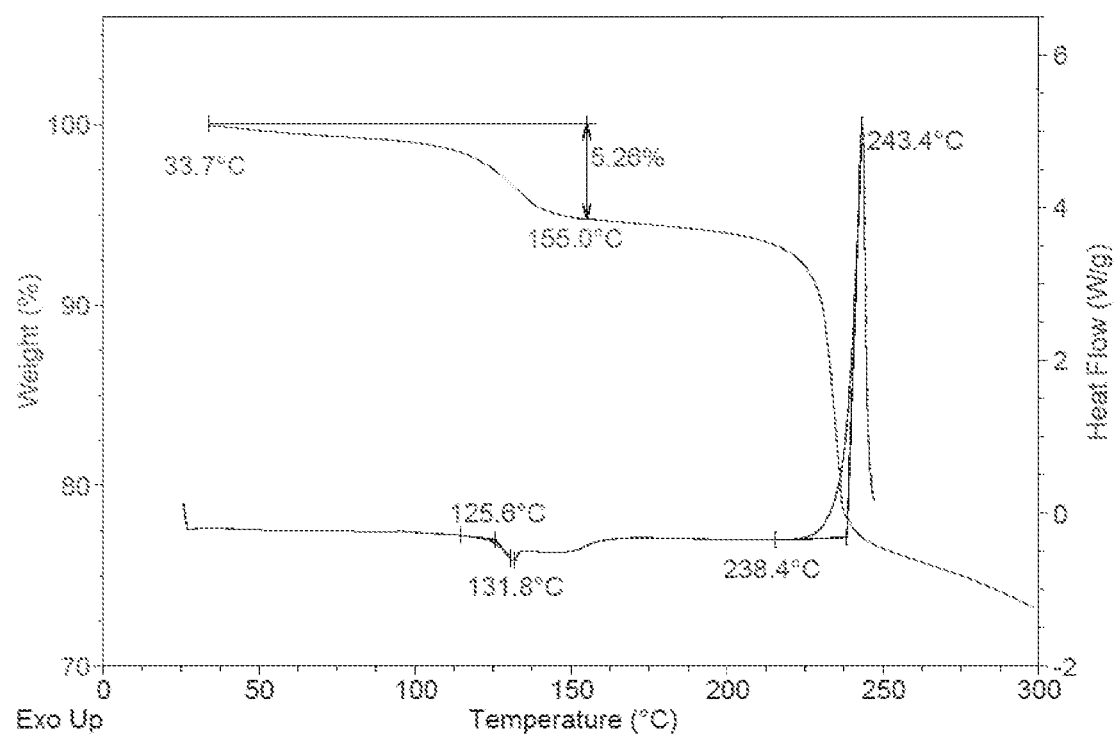
FIG. 3B shows the TGA/DSC curve of Form B.

Preferably, Form B has a DSC substantially in accordance with FIG. 3B, and/or a TGA substantially in accordance with FIG. 3B.

Crystalline Forms of Compound 1 Fumarate (Form C1, C2 and C3)

In yet another embodiment of the first aspect, disclosed herein is a crystalline form of fumarate salt of Compound 1 (i.e., Crystalline form of Compound 1 Fumarate),

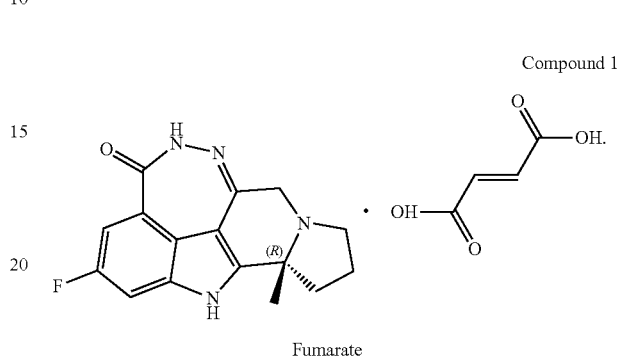

Compound 1 Fumarate

In some embodiments, the Compound 1 Fumarate salt has three crystalline forms (hereinafter Forms C1, C2 and C3).

In some embodiments, Crystalline form of Compound 1 Fumarate is Form C1, which has an X-ray powder diffraction pattern summarized in Table 7.

TABLE 7

X-ray Diffraction Pattern of Form C1

| Peak# | Diffraction angle (2 theta) [°] | d-spacing [Å] | Relative intensity [%] |
|---|---|---|---|
| 1 | 7.122171 | 12.41191 | 100.00 |
| 2 | 9.928316 | 8.90921 | 11.24 |
| 3 | 11.119910 | 7.95705 | 16.25 |
| 4 | 13.474780 | 6.57130 | 6.63 |
| 5 | 14.474450 | 6.11962 | 23.40 |
| 6 | 15.497380 | 5.71792 | 29.33 |
| 7 | 17.470430 | 5.07635 | 35.89 |
| 8 | 18.888540 | 4.69831 | 8.10 |
| 9 | 19.917210 | 4.45792 | 3.66 |
| 10 | 21.988050 | 4.04253 | 18.51 |
| 11 | 22.841530 | 3.89337 | 33.83 |
| 12 | 24.790780 | 3.59149 | 41.18 |
| 13 | 26.187870 | 3.40297 | 22.86 |
| 14 | 26.686220 | 3.34054 | 18.14 |
| 15 | 28.172990 | 3.16754 | 14.29 |
| 16 | 28.807460 | 3.09921 | 76.10 |
| 17 | 29.427250 | 3.03533 | 20.29 |
| 18 | 32.229800 | 2.77751 | 3.56 |
| 19 | 35.852010 | 2.50476 | 4.58 |

In some embodiments, Form C1 is a hydrate.
In some embodiments, Form C2 is a sesqui-hydrate.
In some embodiments, crystalline form of Compound 1 Fumarate is Form C2, characterized by an X-ray powder diffraction pattern comprising diffraction peaks having 2θ angle values independently selected from: approximately 6.4±0.2°, 9.8±0.2°, 13.8±0.2°, and 24.3±0.2°.

In some embodiments, Form C2 is characterized by an X-ray powder diffraction pattern comprising diffraction peaks having 2θ angle values independently selected from: approximately 6.4±0.2°, 9.8±0.2°, 13.4±0.2°, 13.8±0.2°, and 24.3±0.2°.

In some embodiments, Form C2 is characterized by an X-ray powder diffraction pattern comprising diffraction peaks having 2θ angle values independently selected from: approximately 6.4±0.2°, 9.8±0.2°, 13.4±0.2°, 13.8±0.2°, 18.2±0.2°, 24.0±0.2°, 24.3±0.2°, and 28.4±0.2°.

In some embodiments, Form C2 is characterized by an X-ray powder diffraction pattern comprising diffraction peaks having 2θ angle values independently selected from: approximately 6.4±0.2°, 9.8±0.2°, 13.4±0.2°, 13.8±0.2°, 18.2±0.2°, 24.0±0.2°, 24.3±0.2°, 27.8±0.2°, and 28.4±0.2°.

In some embodiments, Form C2 is characterized by an X-ray powder diffraction pattern comprising diffraction peaks having 2θ angle values independently selected from: approximately 6.4±0.2°, 9.8±0.2°, 13.4±0.2°, 13.8±0.2°, 18.2±0.2°, 20.2±0.2°, 24.0±0.2°, 24.3±0.2°, 27.8±0.2°, and 28.4±0.2°.

In some embodiments, Form C2 is characterized by an X-ray powder diffraction pattern comprising diffraction peaks having 2θ angle values independently selected from: approximately 6.4±0.2°, 9.8±0.2°, 13.4±0.2°, 13.8±0.2°, 18.2±0.2°, 19.12±0.2°, 20.2±0.2°, 24.0±0.2°, 24.3±0.2°, 27.8±0.2°, and 28.4±0.2°.

In some embodiments, Form C2 is characterized by an X-ray powder diffraction pattern comprising diffraction peaks having 2θ angle values independently selected from: approximately 6.4±0.2°, 9.8±0.2°, 13.1±0.2°, 13.4±0.2°, 13.8±0.2°, 16.8±0.2°, 18.2±0.2°, 19.12±0.2°, 20.2±0.2°, 22.8±0.2°, 24.0±0.2°, 24.3±0.2°, 26.3±0.2°, 27.8±0.2°, and 28.4±0.2°.

In some embodiments, Form C2 is characterized by an X-ray powder diffraction pattern comprising diffraction peaks having 2θ angle values independently selected from: approximately 6.4±0.2°, 9.8±0.2°, 13.1±0.2°, 13.4±0.2°, 13.8±0.2°, 16.8±0.2°, 17.7±0.2°, 18.2±0.2°, 19.12±0.2°, 20.2±0.2°, 22.8±0.2°, 24.0±0.2°, 24.3±0.2°, 26.3±0.2°, 26.7±0.2°, 27.8±0.2°, 28.4±0.2°, and 29.5±0.2°.

In some embodiments, Form C2 has an X-ray powder diffraction pattern summarized in Table 8.

TABLE 8

X-ray Diffraction Pattern of Form C2

| Peak# | Diffraction angle (2 theta) [°] | d-spacing [Å] | Relative intensity [%] |
|---|---|---|---|
| 1 | 3.283158 | 26.91158 | 37.60 |
| 2 | 6.402161 | 13.80610 | 52.28 |
| 3 | 9.753031 | 9.06894 | 70.40 |
| 4 | 13.080440 | 6.76850 | 13.76 |
| 5 | 13.475960 | 6.57072 | 52.17 |
| 6 | 13.822190 | 6.40690 | 100.00 |
| 7 | 16.819030 | 5.27146 | 18.96 |
| 8 | 17.746420 | 4.99802 | 12.35 |
| 9 | 18.182220 | 4.87920 | 40.31 |
| 10 | 19.073040 | 4.65327 | 21.18 |
| 11 | 20.254770 | 4.38438 | 22.54 |
| 12 | 22.824110 | 3.89631 | 15.98 |
| 13 | 23.444980 | 3.79451 | 9.99 |
| 14 | 24.099390 | 3.69293 | 47.36 |
| 15 | 24.349990 | 3.65549 | 67.45 |
| 16 | 25.476000 | 3.49642 | 9.82 |
| 17 | 26.297070 | 3.38909 | 15.07 |
| 18 | 26.698480 | 3.33904 | 14.88 |
| 19 | 27.846030 | 3.20399 | 30.43 |
| 20 | 28.430350 | 3.13945 | 41.53 |
| 21 | 29.568750 | 3.02113 | 11.92 |
| 22 | 32.618110 | 2.74532 | 7.82 |

Figure 5A:
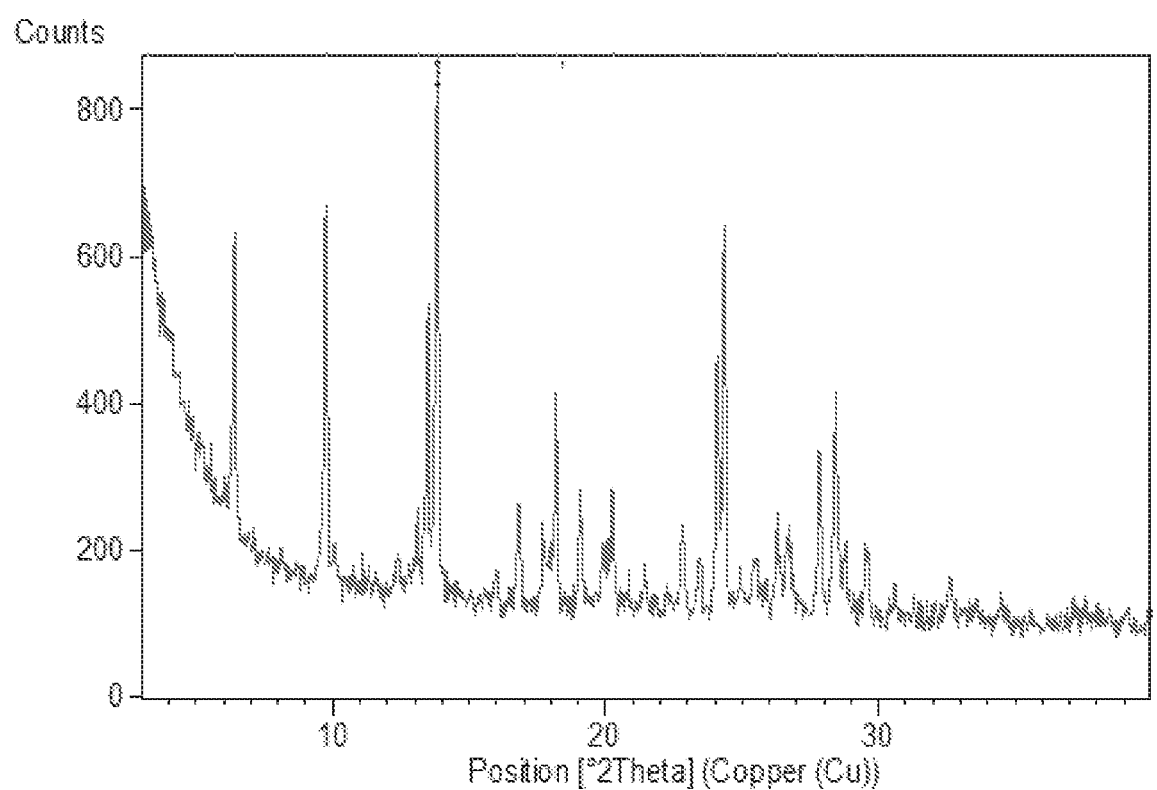
FIG. 5A shows the XRPD pattern of Form C2 of Example 4.

In some embodiments, Form C2 has an X-ray powder diffraction pattern substantially in accordance with FIG. 5A.

Figure 5B:
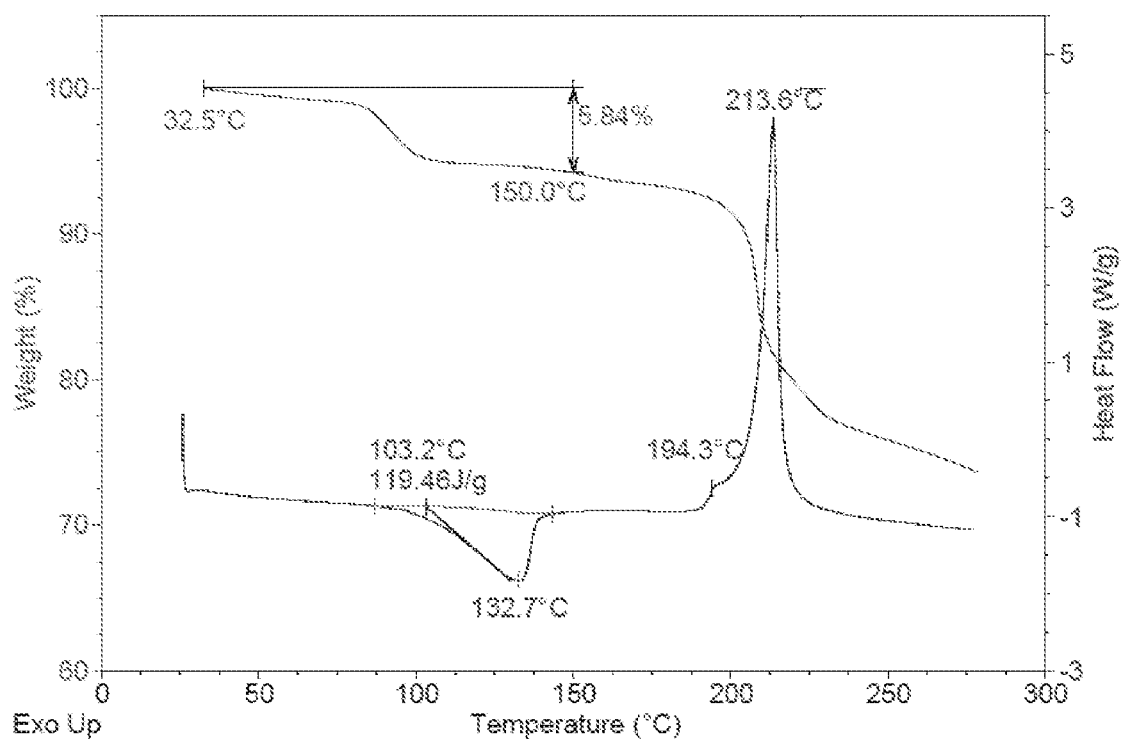
FIG. 5B shows the TGA/DSC curve of Form C2 of Example 4.

Preferably, Form C2 has a DSC substantially in accordance with FIG. 5B, and/or a TGA substantially in accordance with FIG. 5B.

Method of Preparing Crystalline Forms

Also disclosed herein is a method of preparing a crystalline form of a salt of Compound 1, comprising slurrying a suspension of Crystalline Sesqui-Hydrate of Compound 1 and an acid or anhydride thereof in a solvent at a certain temperature for a certain duration of time to obtain the desired crystalline form.

In some embodiments, the molar ratio of Crystalline Sesqui-Hydrate of Compound 1 and the acid is about 1. In some embodiments, the acid is $H_3PO_4$ or maleic acid or fumaric acid or anhydride thereof. In some embodiments, the solvent is ethyl acetate, acetone, acetonitrile, Isopropanol/$H_2O$ (19:1, v:v) or a mixture thereof. In some embodiments, the temperature for slurrying is room temperature (25±3° C.). In some embodiments, the duration of time for slurrying is about 1 hour to 3 days or longer; preferably about 1 day to 3 days. In some embodiments, the crystalline form is Form A, Form B, Form C1 or Form C2. In some embodiments, the solvent is Acetone, ACN or Isopropanol/$H_2O$ (19:1, v:v) and the crystalline form the crystalline form is Form A. In some embodiments, the solvent Acetone, ACN or Isopropanol/$H_2O$ (19:1, v:v) and the crystalline form is From B. In some embodiments, the solvent is Isopropanol/$H_2O$ (19:1, v:v) and the crystalline form is Form C2. In some embodiments, the method further comprising: adding a crystal seed of the desired crystalline form into the suspension before or during slurrying. In some embodiments, slurrying is accompanied with stirring the suspension. In some embodiments, the suspension is formed by adding the solvent into the mixture of Crystalline Sesqui-Hydrate of Compound 1 and the acid or anhydride thereof.

EXAMPLES

The present invention is further exemplified, but not limited, by the following examples that illustrate the invention. In the examples of the present invention, the techniques or methods, unless expressly stated otherwise, are conventional techniques or methods in the art.

Example 1: Preparation of Crystalline Sesqui-Hydrate of Compound 1

Crystalline Sesqui-Hydrate of Compound 1 was disclosed in the unpublished PCT application PCT/CN2016/096200, the entire contents of which are incorporated herein by reference.

Scheme 1: Synthetic Process of Compound 1 (freebase) in a large scale

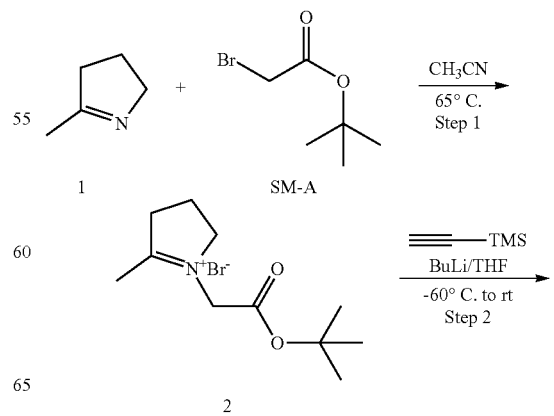

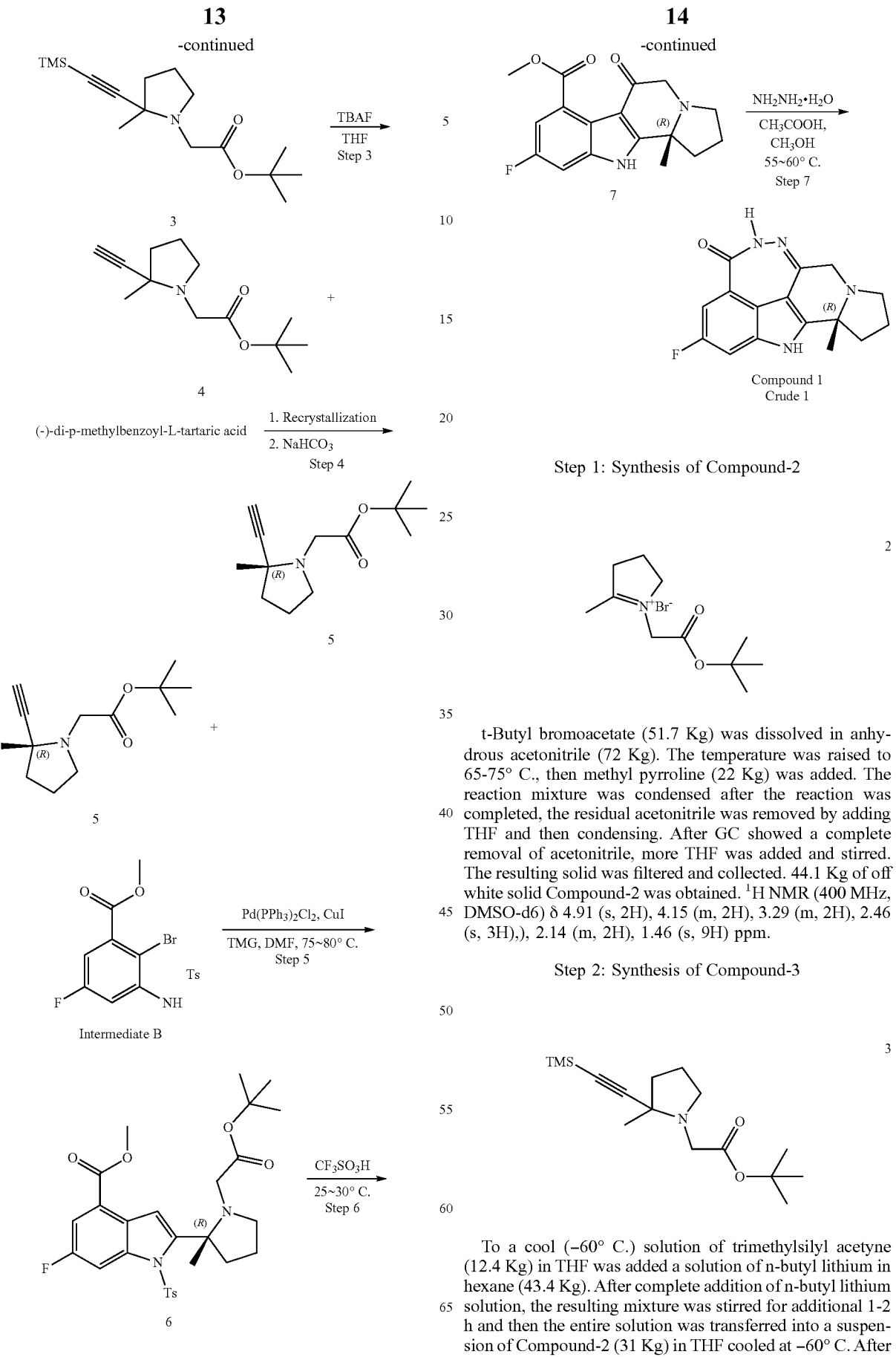

t-Butyl bromoacetate (51.7 Kg) was dissolved in anhydrous acetonitrile (72 Kg). The temperature was raised to 65-75° C., then methyl pyrroline (22 Kg) was added. The reaction mixture was condensed after the reaction was completed, the residual acetonitrile was removed by adding THF and then condensing. After GC showed a complete removal of acetonitrile, more THF was added and stirred. The resulting solid was filtered and collected. 44.1 Kg of off white solid Compound-2 was obtained. $^1$H NMR (400 MHz, DMSO-d6) δ 4.91 (s, 2H), 4.15 (m, 2H), 3.29 (m, 2H), 2.46 (s, 3H),), 2.14 (m, 2H), 1.46 (s, 9H) ppm.

Step 2: Synthesis of Compound-3

To a cool (−60° C.) solution of trimethylsilyl acetyne (12.4 Kg) in THF was added a solution of n-butyl lithium in hexane (43.4 Kg). After complete addition of n-butyl lithium solution, the resulting mixture was stirred for additional 1-2 h and then the entire solution was transferred into a suspension of Compound-2 (31 Kg) in THF cooled at −60° C. After transfer completion, the resulting mixture was warmed to room temperature and stirred for 1 h. The reaction was quenched with water, extracted with petroleum. The organic phase was washed with brine, dried over sodium sulfate, condensed to give 25.1 Kg of Compound-3. $^1$H NMR (400 MHz, DMSO-d6) δ 3.34 (d, J=16.0 Hz, 1H), 3.15 (m, 1H), 2.78 (d, J=16.0 Hz, 1H), 2.27 (m, 1H), 1.93 (m, 1H), 1.68 (m, 3H), 1.41 (s, 9H), 1.24 (s, 3H), 0.13 (s, 9H) ppm.

Step 3: Synthesis of Compound-4

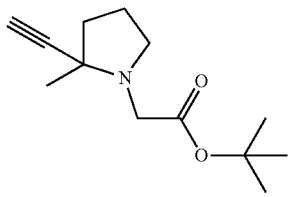

4

To a cool (0-5° C.) solution of 70.1 Kg of Compound-3 in THF was added tetrabutylammonium fluoride (13.3 Kg) in THF. After de-silylation was completed, the reaction was quenched with water, extracted with petroleum (290 Kg) and the organic phase was condensed and passed through a pad of silica gel. The filtrate was condensed to give 48 Kg of Compound-4. $^1$H NMR (400 MHz, DMSO-d6) δ 3.36 (d, J=16.0 Hz, 1H), 3.15 (m, 1H), 2.82 (d, J=16.0 Hz, 1H), 2.28 (m, 1H), 1.97 (m, 1H), 1.70 (m, 3H), 1.41 (s, 9H), 1.26 (s, 3H) ppm.

Step 4: Syntheses of Compound-5

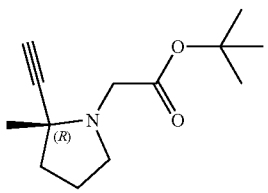

5

A solution of Compound-4 (48 Kg) in THF was warmed to 50-60° C. To the above solution was added a solution of (−)-di-p-methylbenzoyl-L-tartaric acid (69.6 Kg) in THF. The resulting mixture was stirred at 50-60° C. 1-2 h and then gradually cooled to 0-10° C. The resulting salt solid was filtered and re-suspended in methyl tert-butyl ether and heated at 50-60° C. for 1 h. The mixture was gradually cooled to 0-5° C. The resulting solid was filtered to give 13.1 Kg of off-white solid. The solid was treated with aqueous sodium hydroxide, extracted with petroleum, condensed to give 13.1 Kg of Compound-5 (ee≥96%). $^1$H NMR (400 MHz, DMSO-d6) δ 3.36 (d, J=16.0 Hz, 1H), 3.15 (m, 1H), 2.82 (d, J=16.0 Hz, 1H), 2.29 (m, 1H), 1.97 (m, 1H), 1.70 (m, 3H), 1.41 (s, 9H), 1.26 (s, 3H) ppm.

Step 5: Syntheses of Compound-6

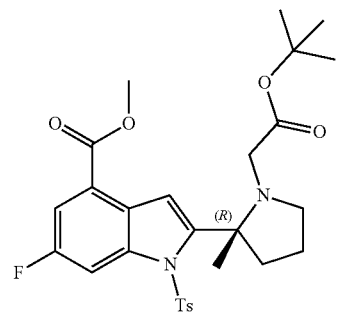

6

Intermediate B (14 Kg), bis(triphenyl)palladium dichloride (0.7 Kg), CuI (0.42 Kg) and tetramethyl guanidine (11.5 Kg) were dissolved in DMF (48.1 Kg). The resulting solution was stirred and de-gassed and then heated under nitrogen. A solution of Compound-5 (9.24 Kg) in DMF (16 Kg) was added dropwise. After coupling, the organic phase was condensed, the residue was stirred with water (145 Kg) and methyl t-butyl ether (104 Kg), the entire mixture passed trough a pad of celite, separated. The organic phase was washed with a solution of thiourea (14 Kg) in water (165 kg) and brine (100 Kg), condensed. The residue was dissolved in a mixture of n-heptane (120 Kg) and ethyl acetate (28 Kg). The solution was mixed with charcoal (1.4 kg), heated at 40-50° C. for 1-2 h, filtered though a pad of silica gel. The filtrate was condensed to give Compound-6 solid (14.89 Kg) and the liquid filtrate (13 Kg heptane solution, contains 1.24 Kg of Compound-6). $^1$H NMR (400 MHz, DMSO-d6) δ 7.85 (d, J=9.6 Hz, 1H), 7.55 (m, 3H), 7.32 (m, 2H), 3.87 (s, 3H), 3.37 (d, J=16.0 Hz, 1H), 3.22 (m, 1H), 2.94 (d, J=16.0, Hz, 1H), 2.60 (m, 1H), 2.48 (m, 1H), 2.29 (s, 3 h), 2.26 (m, 1H), 1.82 (m, 2H), 1.49 (s, 3H), 1.43 (s, 9H) ppm.

Step 6: Syntheses of Compound-7

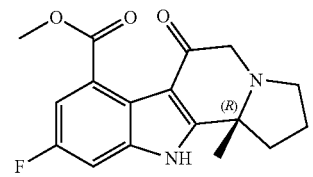

7

The above heptane solution of Compound-6 was added into a cold trifluoromethane sulfonic acid (66.1 Kg) while maintaining the internal temperature below 25° C. Then solid Compound-6 (14.87 Kg) was added batchwise. After complete addition of Compound-6, the reaction mixture was warmed to 25-30° C. and stirred until the reaction was completed. The entire mixture was poured into a solution of sodium acetate (123.5 Kg) in water (240 Kg). pH of the solution was then adjusted to 7-8 by adding solid potassium carbonate (46.1 Kg). The mixture was extracted with dichloromethane (509 Kg), condensed. The residue was mixed with n-heptane (41 Kg), condensed again to give the precipitate which was filtered and washed by n-heptane (8 Kg) and dried. 8.78 Kg of Compound-7 was obtained. $^1$H NMR (400 MHz, DMSO-d6) δ 12.30 (s, 1H), 7.35 (dd, J=9.2, 1.6 Hz, 1H), 7.08 (dd, J=9.2, 1.6 Hz, 1H), 3.79 (s, 3H), 3.68 (d, J=17.2 Hz, 1H), 3.21 (d, J=17.2 Hz, 1H), 3.06 (m, 1H), 2.68 (m, 1H), 1.96 (m, 1H), 1.74 (m, 1H), 1.49 (s, 3H) ppm.

Step 7: Syntheses of Compound 1-Crude 1

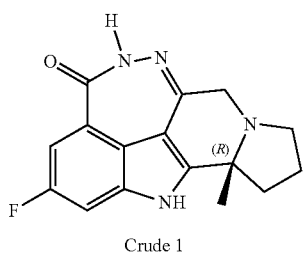

Crude 1

Compound-7 (8.76 Kg) was dissolved in methanol (69 Kg) and internally cooled below 25° C. Acetic acid (9.3 Kg) and hydrazine hydrate (7.4 Kg, 85%) were added while maintaining internal temperature below 25° C. After degassed and re-filled with nitrogen (repeated three times), the reaction mixture was stirred at 55-60° C. for 4 h. After a complete reaction, the mixture was mixed with water (29 Kg). The organic phase was condensed and potassium carbonate (12.5 Kg) in water (40 Kg) was added. The resulting solid was filtered, washed with water (18.3 Kg). The solid was slurred with water (110 Kg), centrifuged, dried and slurred with ethanol (9.4 Kg), centrifuged, filtered, washed with ethanol, dried in vacuum to give Compound 1-Crude 1 (7.91 Kg). $^1$H-NMR (600 MHz, DMSO-d$_6$) δ 12.0 (s, 1H), 10.2 (s, 1H), 7.31 (dd, 1H, J=9.6, 2.0 Hz), 7.19 (dd, 1H, J=9.6, 2.0 Hz), 3.77 (d, 1H, J=16.4 Hz), 3.34 (d, 1H, J=16.4 Hz), 2.97-3.02 (m, 1H), 2.54-2.58 (m, 1H), 2.35-2.40 (m, 1H), 1.90-1.94 (m, 1H), 1.73-1.75 (m, 1H), 1.47 (s, 3H), 1.43-1.45 (m, 1H) ppm. MS (ESI) m/e [M+1]$^+$ 299.

Step 8: Synthesis of Compound 1-Crude 2

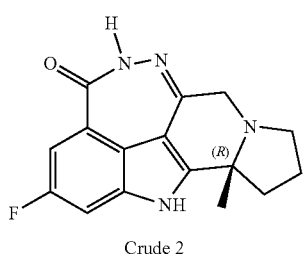

Crude 2

Under nitrogen protection, Compound 1 (Crude 1) (7.88 Kg) was stirred with isopropanol (422 Kg) and heated at 70-80° C. for 1-2 h until the solid disappeared completely. A solution of (+)-di-p-methylbenzoyl-D-tartaric acid (10.25 Kg) in isopropanol (84.4 Kg) was added. The mixture was stirred for 14-16 h, filtered and washed with isopropanol (16 Kg), dried. The resulting salt was added into a stirred solution of potassium carbonate (6.15 Kg) in water (118 Kg). The precipitate was centrifuged, filtered, washed with water (18 Kg). The solid was slurred with water (110 Kg), centrifuged, dried. The solid was dissolved in THF (75 Kg), active carbon (0.8 Kg) was added. The mixture was degassed and re-protected by nitrogen, stirred and heated at 40-45° C. for 1-2 h, cooled, filtered through celite, condensed to give the solid which was further slurred with ethanol (6.5 Kg), filtered to give 5.6 Kg of Compound 1 crude 2. $^1$H NMR (400 MHz, DMSO-d6) δ 12.0 (s, 1H), 10.2 (s, 1H), 7.31 (dd, 1H, J=9.6, 2.0 Hz), 7.19 (dd, 1H, J=9.6, 2.0 Hz), 3.77 (d, 1H, J=16.4 Hz), 3.34 (d, 1H, J=16.4 Hz), 2.97-3.02 (m, 1H), 2.54-2.58 (m, 1H), 2.35-2.40 (m, 1H), 1.90-1.94 (m, 1H), 1.73-1.75 (m, 1H), 1.47 (s, 3H), 1.43-1.45 (m, 1H) ppm. MS (ESI) m/e [M+1]$^+$ 299.

Step 9: Preparation of Crystalline Sesqui-Hydrate of Compound 1

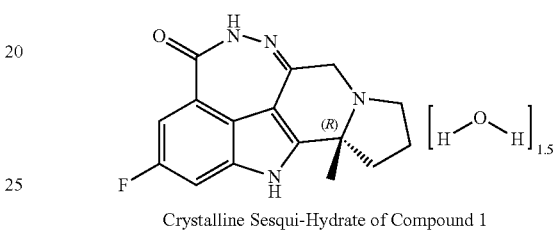

Crystalline Sesqui-Hydrate of Compound 1

Compound 1-Crude 2 (5.3 Kg) was mixed with a solution of isopropanol (41.6 Kg) and water (15.9 Kg). The mixture was degassed and re-protected under nitrogen and then heated to 60° C. and stirred for 2-4 h until the solid was dissolved completely. The temperature was raised to 70-80° C. and water (143 Kg) was added. The resulting mixture was heated to the internal temperature of 70-80° C. and then the heating was stopped but stirred gently for 16 h. The precipitate was filtered, washed with water (19 Kg) and slurred with water (21 kg) for 2 h. The resulting solid was filtered, washed with water (20 Kg). The filtered solid was dried at the temperature below 45° C. for 24-36 h, to obtain a crystal product (4.22 kg).

Figure 1A:
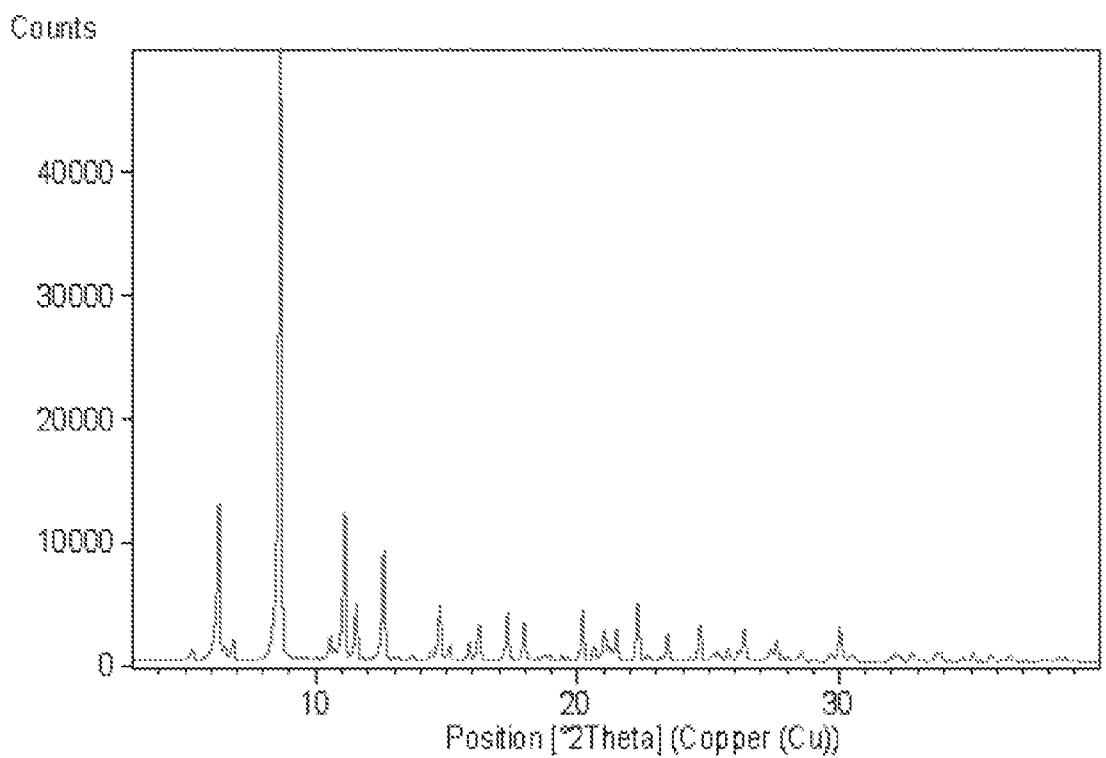
FIG. 1A shows the XRPD pattern of Crystalline Sesqui-Hydrate of Compound 1.
Figure 1B:
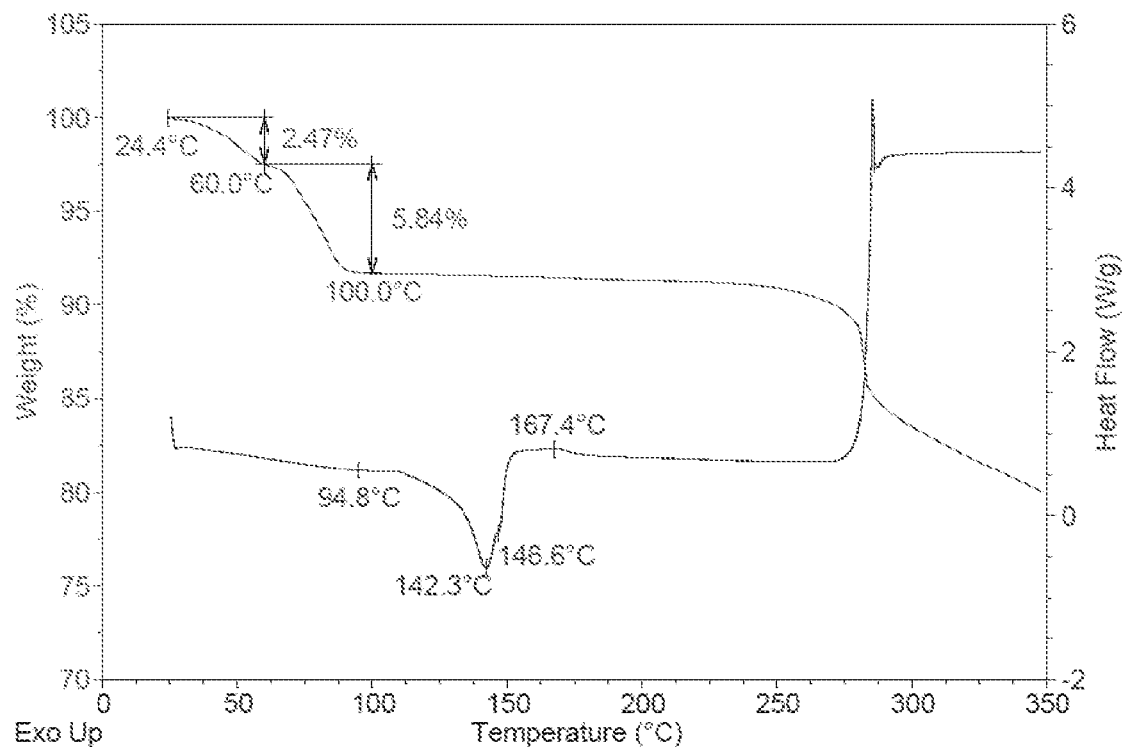
FIG. 1B shows the TGA/DSC curves of Crystalline Sesqui-Hydrate of Compound 1.
Figure 1C:
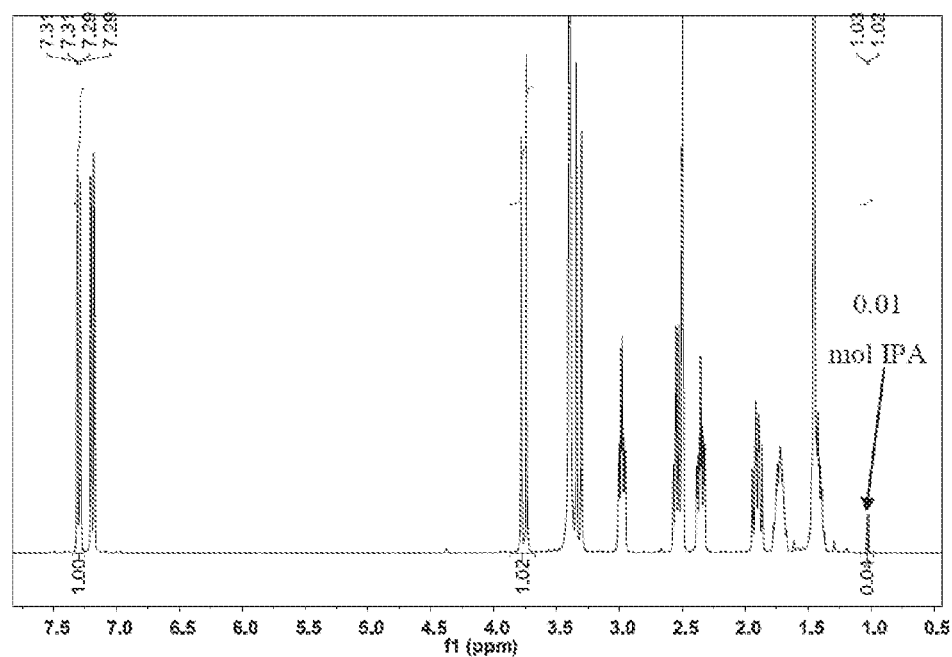
FIG. 1C shows the $^1$H-NMR of Crystalline Sesqui-Hydrate of Compound 1.

The XRPD pattern in FIG. 1A confirms the crystalline structure of the resultant Crystalline Sesqui-Hydrate of Compound 1. The TGA/DSC curves of Crystalline Sesqui-Hydrate of Compound 1 was shown in FIG. 1B, wherein 0.5 water molecule is lost at about 60° C. and another 1.0 water molecule is lost at 100° C., confirming the molar number of water in the crystalline form is 1.5. The $^1$H-NMR for Crystalline Sesqui-Hydrate of Compound 1 was shown in FIG. 1C.

The quantitative elemental analysis of Crystalline Sesqui-Hydrate of Compound 1 is presented in Table 9. The absolute difference of C, H, N content found and calculated is below 0.3% and is consistent with its molecular formula, $C_{16}H_{15}FN_4O \cdot 1.5H_2O$. Analysis was performed in duplicate.

TABLE 9

Quantitative Elemental Analysis of Crystalline Sesqui-Hydrate of Compound 1

| Analysis | Theory (%) | Found (%) | Absolute Difference (%) |
|---|---|---|---|
| C | 59.07 | 59.05 | 0.02 |
| H | 5.58 | 5.59 | 0.01 |
| N | 17.22 | 17.48 | 0.26 |

Example 2: Preparation of Crystalline form of Compound 1 Phosphate (Form A)

23.0 μL of concentrated $H_3PO_4$ (85%) was diluted with 3.0 mL of Isopropanol/$H_2O$ (19:1, v:v), and then was added into about 100 mg of Crystalline Sesqui-Hydrate of Compound 1 in a 20 mL glass vial. The resultant mixture or suspension was slurried at RT for about 1 day, to obtain 104.5 mg of the desired crystalline form (yield 79.0%).

The stoichiometry ratio (acid/Compound 1) of Form A was 1.0 according to the result of HPLC/IC. The XRPD pattern was used to characterize Form A; see FIG. 2A.

Figure 2D:
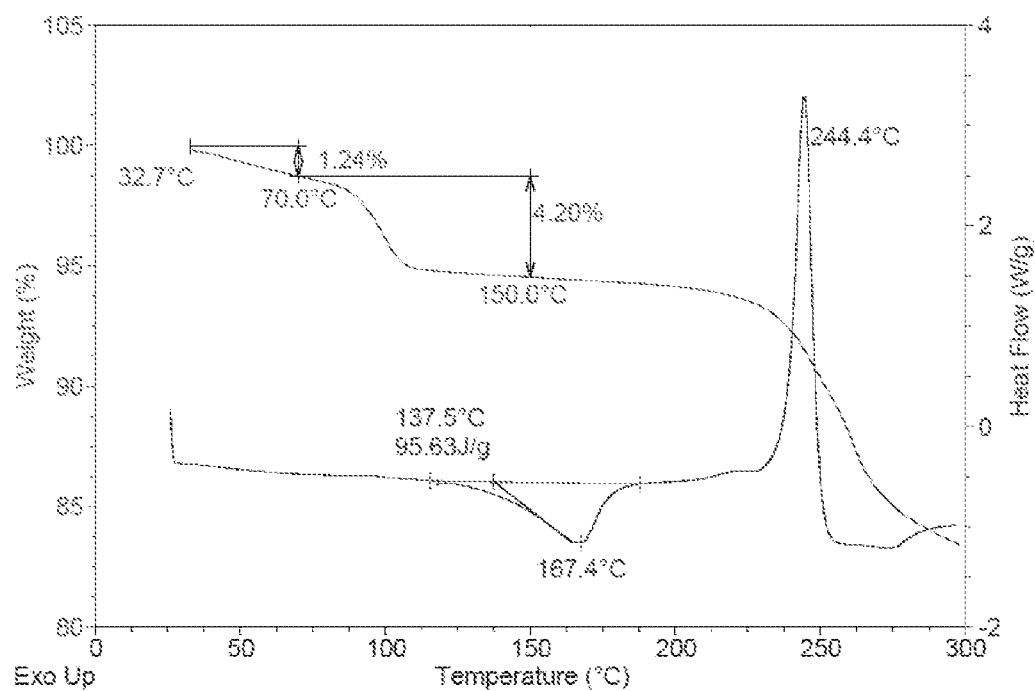
FIG. 2D shows the TGA/DSC curves of the heated Form A (170° C.).

The TGA/DSC curves in FIG. 2B showed a weight loss of 5.5% before 150° C. with multiple thermal events followed by a sharp exotherm at 239.2° C. (onset temperature). No form change was observed for Form A after being heated to 170° C. and cooled at ambient conditions showed by XRPD pattern; see FIG. 2C. The TGA/DSC curves of the heated sample in FIG. 2D showed a two-step weight loss of 1.2% and 4.2% before 150° C. with multiple thermal events before decomposition, which were similar with initial Form A sample, indicating that Form A was a hydrate, with the bounded water content close to calculated water content of mono-hydrate (4.3%).

Example 3: Preparation of Crystalline Form of Compound 1 Maleate (Form B)

3.0 mL of Isopropanol/$H_2O$ (19:1, v:v) was added into about 200 mg of Crystalline Sesqui-Hydrate of Compound 1 and maleic acid (1.0 molar equiv.) in a 20 mL glass vial to form a suspension, which was slurried at RT for about 1 day, to obtain 255.4 mg of the desired crystalline form (yield 91.9%).

The XRPD pattern was used to characterize the product as Form B. The TGA/DSC curves in FIG. 3B showed a weight loss of 5.3% before 160° C. and a small endotherm at 131.8° C. (peak temperature), which were speculated to be caused by the removal of residual solvent (0.1 mol equiv. Isopropanol, 1.4%) and maleic acid (melting point ~135° C.).

Figure 3C:
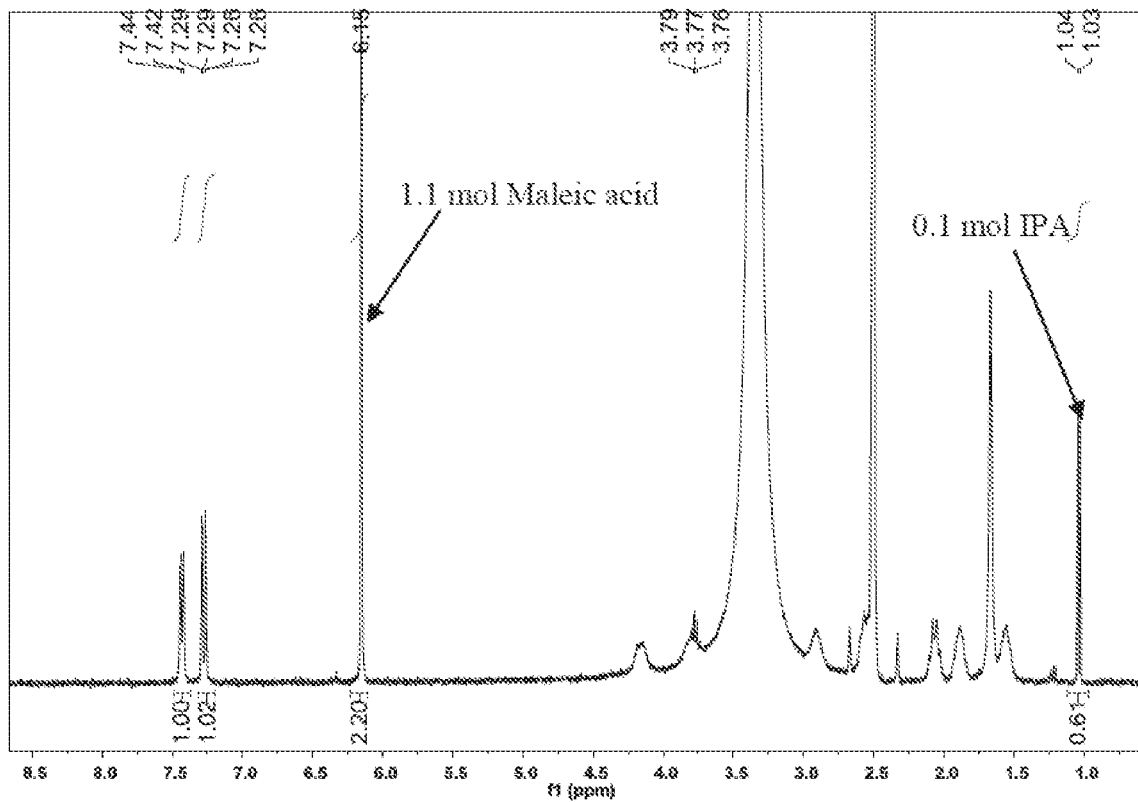
FIG. 3C shows the $^1$H-NMR of Form B.

The stoichiometry ratio (acid/Compound 1) of Form B was detected to be 1.1 by solution NMR, see FIG. 3C.

Figure 3D:
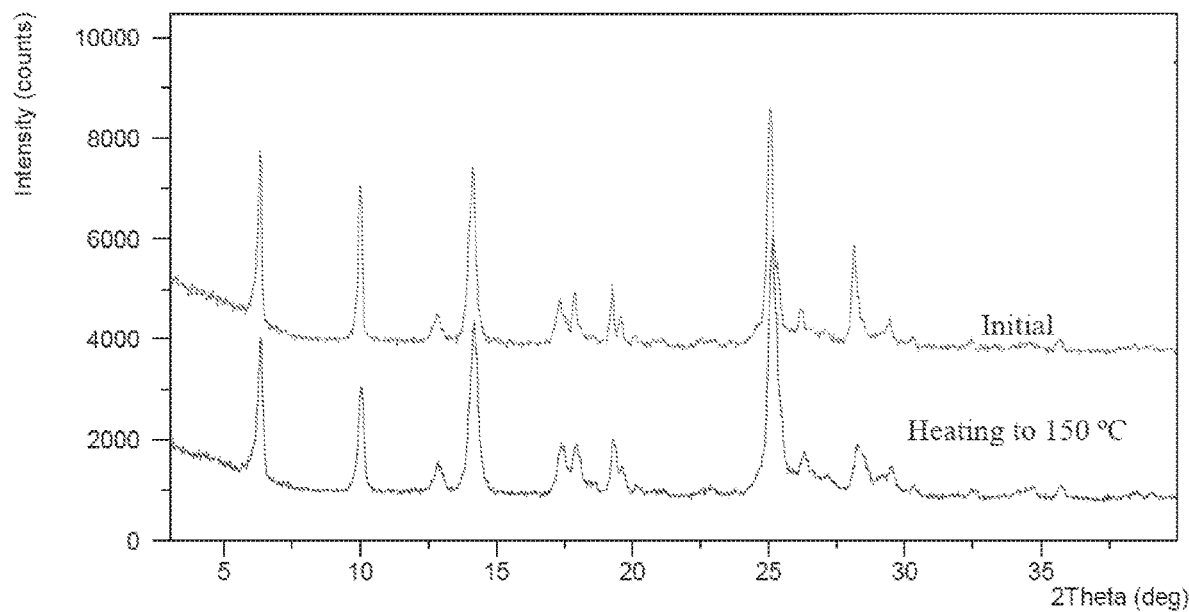
FIG. 3D shows the XRPD patterns overlay of Form B before and after heating (150° C.).
Figure 3E:
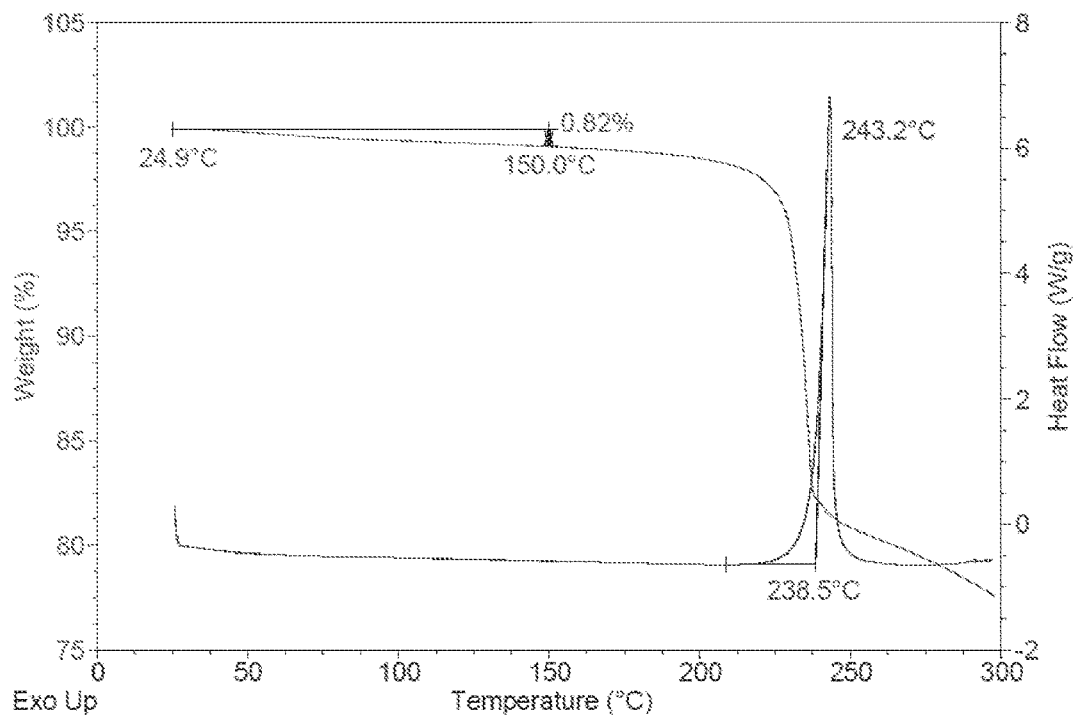
FIG. 3E shows the TGA/DSC curves of the heated Form B (150° C.).
Figure 4A:
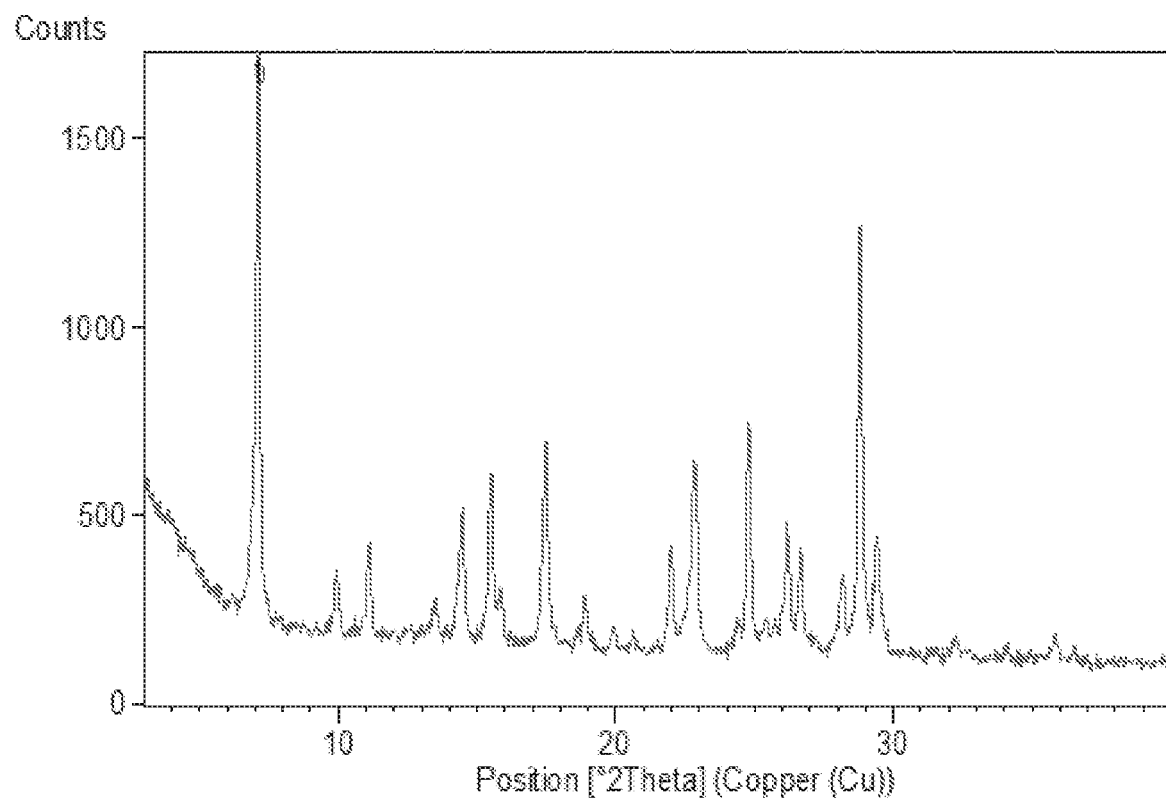
FIG. 4A shows the XRPD pattern of Form C1.
Figure 4B:
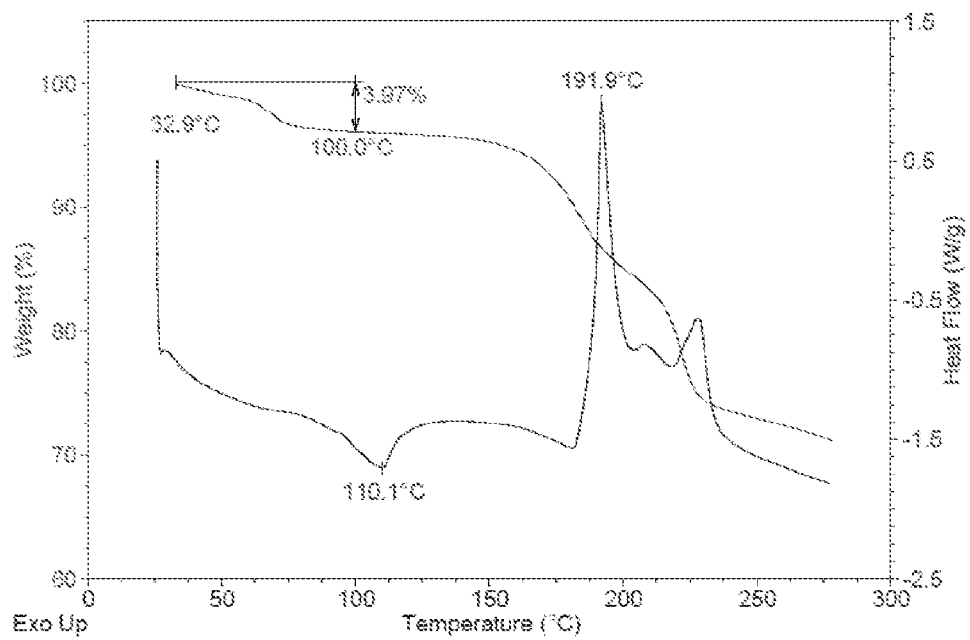
FIG. 4B shows the TGA/DSC curve of Form C1.
Figure 4C:
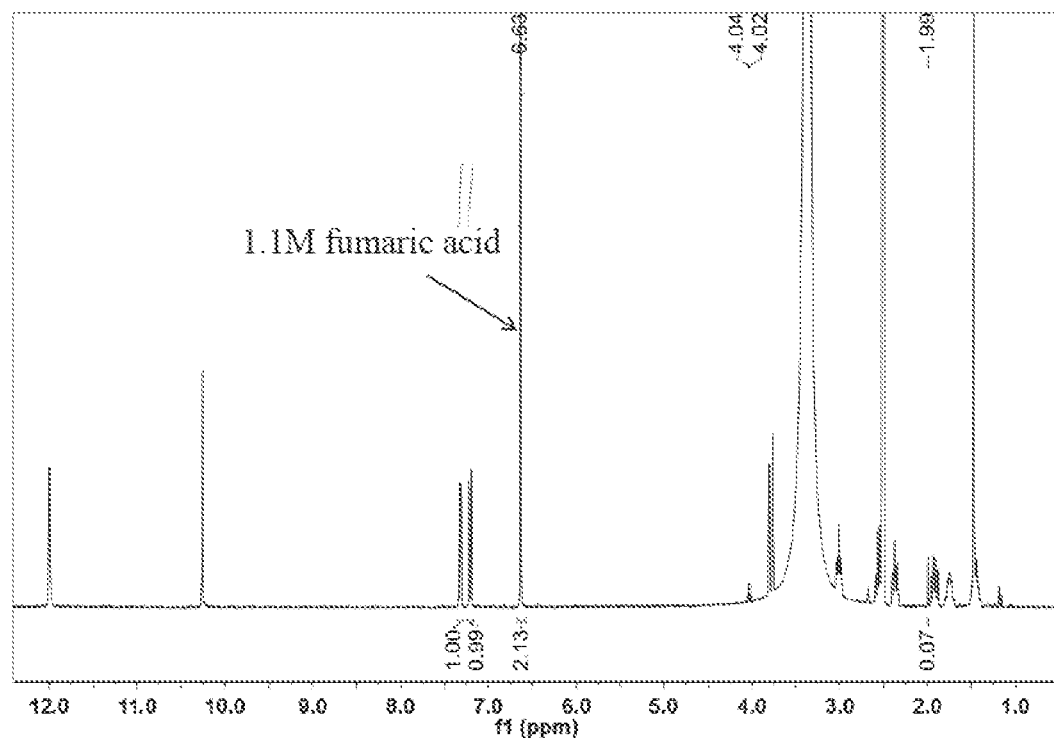
FIG. 4C shows the $^1$H-NMR of Form C1.

No form change was observed for Form B after being heated to 150° C. and cooled at ambient conditions showed by XRPD pattern; see FIG. 3D. The TGA/DSC curves in FIG. 3E showed a minor weight loss and no thermal signals observed before decomposition. Associated with the results of TGA/DSC and solution NMR, Form B was confirmed to be an anhydrate.

Example 4: Preparation of Crystalline Form of Compound 1 Fumarate (Form C2)

THF solution of Crystalline Sesqui-Hydrate of Compound 1 (about 25 mg) was added into a 1.5-mL vial and evaporated to dryness at RT. About 9.8 mg fumaric acid and 0.4 mL of Isopropanol/$H_2O$ (19:1, v/v) were added into the vial and stirred at RT for two days. The desired crystalline was isolated by centrifugation.

The XRPD pattern was used to characterize Form C2; see FIG. 5A.

The TGA/DSC curves in FIG. 5B showed 5.8% weight loss up to 150° C. and a broad endothermic peak at 132.7° C. before decomposition at 213.6° C. (peak temperature), which indicated that Form C2 was peculated to be a hydrate form.

Figure 5C:
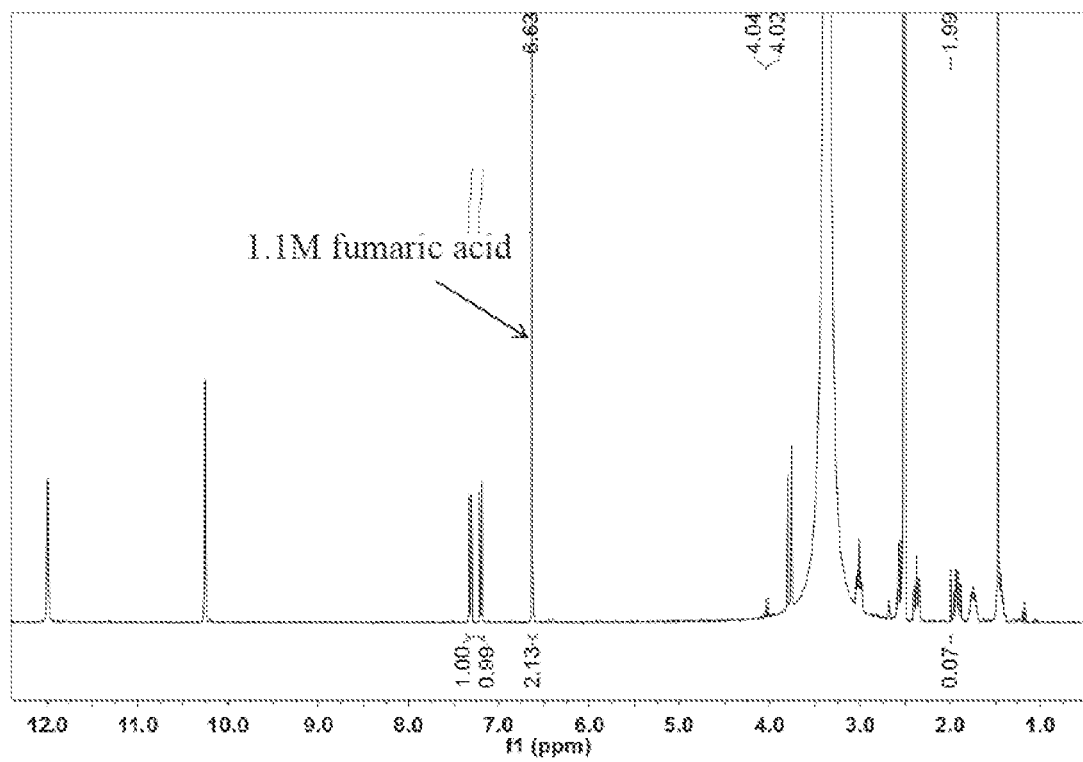
FIG. 5C shows the $^1$H-NMR of Form C2 of Example 4.

The stoichiometry ratio (acid/Compound 1) of Form C2 was determined to be 1.0 by $^1$H NMR spectrums; see FIG. 5C.

Interestingly, the inventors found that when the above solvent (Isopropanol/$H_2O$) was changed to EtOAC or Acetone, a different crystalline form was obtained (referred to as Form C1). The XRPD pattern of Form C1 was showed in FIG. 4A. The TGA/DSC curve of Form C1 was showed in FIG. 4B, wherein Form C1 showed 4.0% weight loss before 100° C. with broad endothermic peak at 110.1° C. before decomposition at 191.9° C. (peak temperature). In addition, the stoichiometry ratio was determined to be 1.1 for Form C1 by $^1$H NMR spectrums shown in FIG. 4C. Form C1 was also speculated to be a hydrate. Compared with Form C1, Form C2 showed higher temperature of dehydration and more regular thermal signals.

The effect of the solvent used for slurry on the resultant crystalline form was also studied as shown in the following table.

| | | Solvent | | | |
|---|---|---|---|---|---|
| | Acid | EtOAc | Acetone | Acetonitrile | Isopropanol:$H_2O$ (19:1, v/v) |
| 1 | *$H_3PO_4$ | Form A | Form A | Form A | Form A |
| 2 | *Maleic acid | Form B + Crystalline Sesqui-Hydrate of Compound 1 | Form B | Form B | Form B |
| 3 | *Fumaric acid | Form C1 | Form C1 | Form C1 + Form C2 | Form C2 |

*the molar ratios of compound 1 and acid for all the acids are 1:1.

Example 5: Alternative Preparation of Crystalline Form of Compound 1 Fumarate (Form C2)

3.0 mL of Isopropanol/$H_2O$ (19:1, v:v) was added into about 200 mg of Crystalline Sesqui-Hydrate of Compound 1 and fumaric acid (1.0 molar equiv.) in a 20 mL glass vial to form a suspension, which was slurried at RT for 1 day, then added the crystalline form (Form C2) prepared in Example 4 as crystal seed into the glass vial, and slurried at RT for another 2 days, to obtain 254.2 mg of the desired crystalline form (yield 91.5%).

Figure 6A:
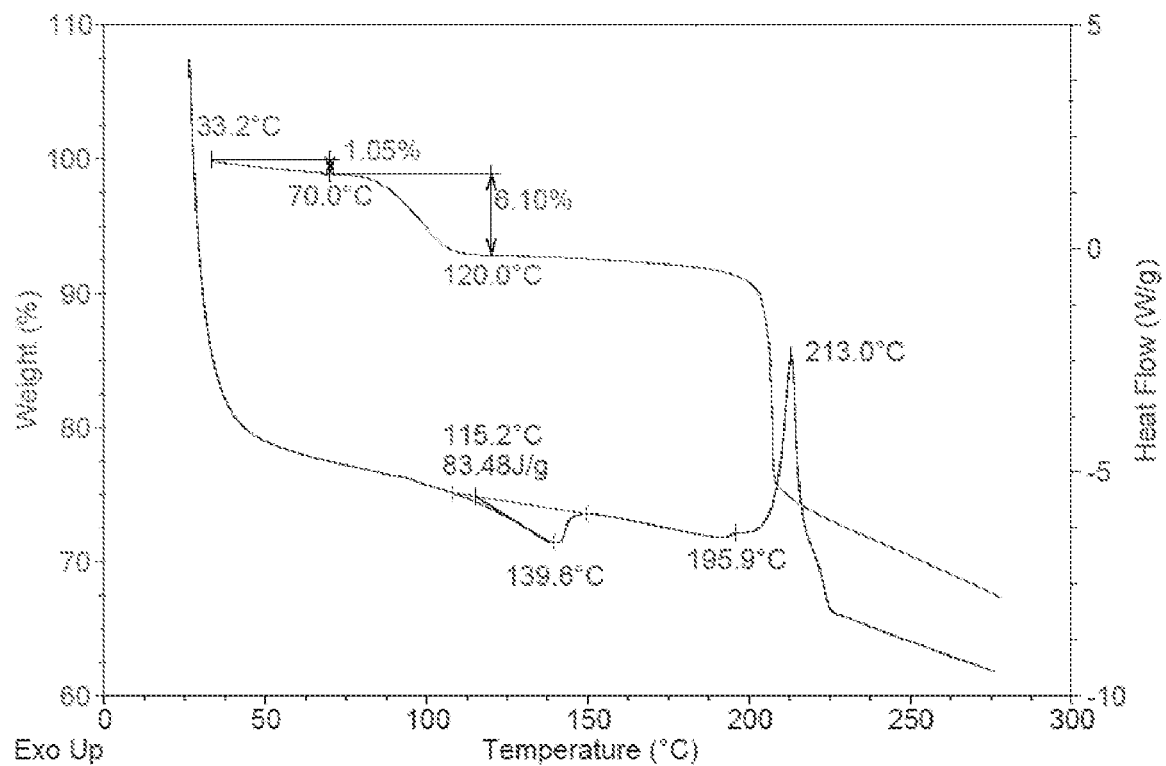
FIG. 6A shows the TGA/DSC curve of Form C2 of Example 5.
Figure 6B:
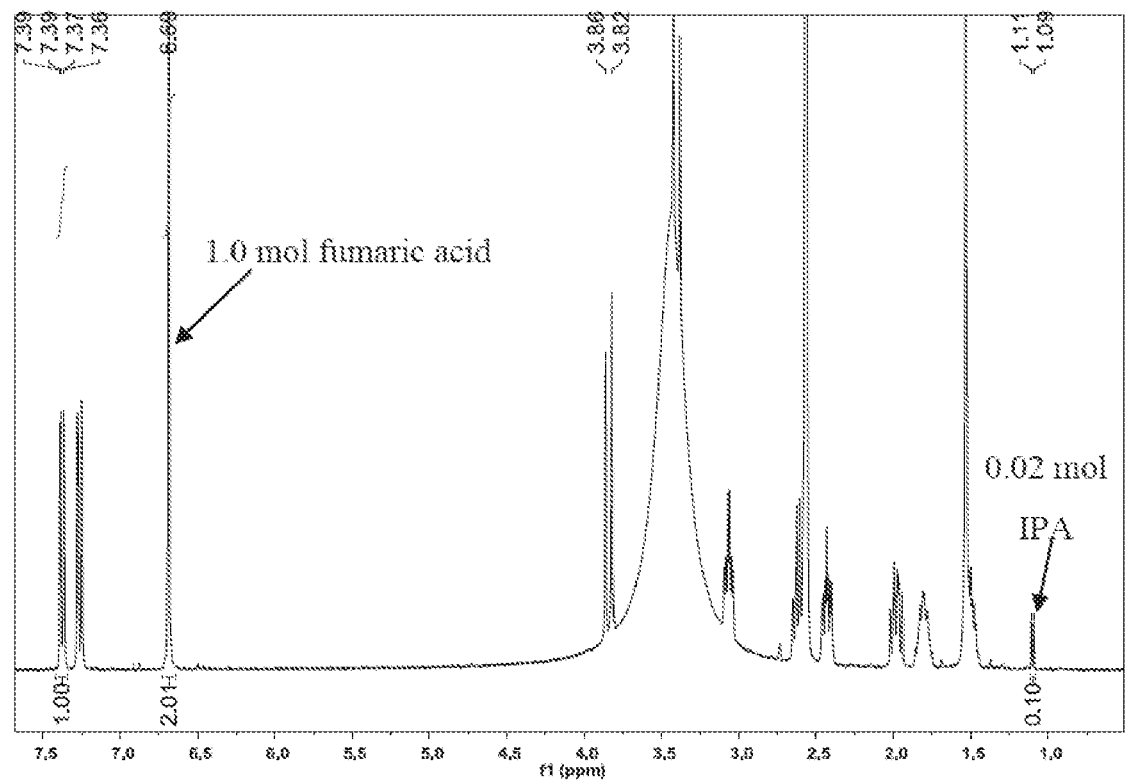
FIG. 6B shows the $^1$H-NMR of Form C2 of Example 5.
Figure 6C:
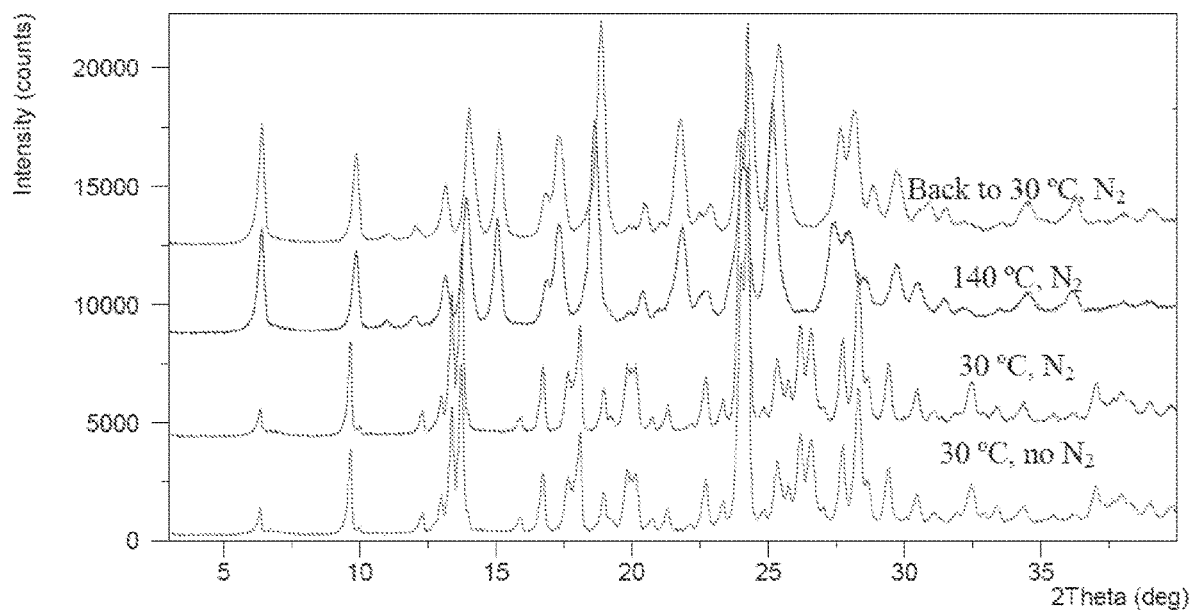
FIG. 6C shows the VT-XRPD patterns overlay of Form C2 of Example 5.
Figure 6D:
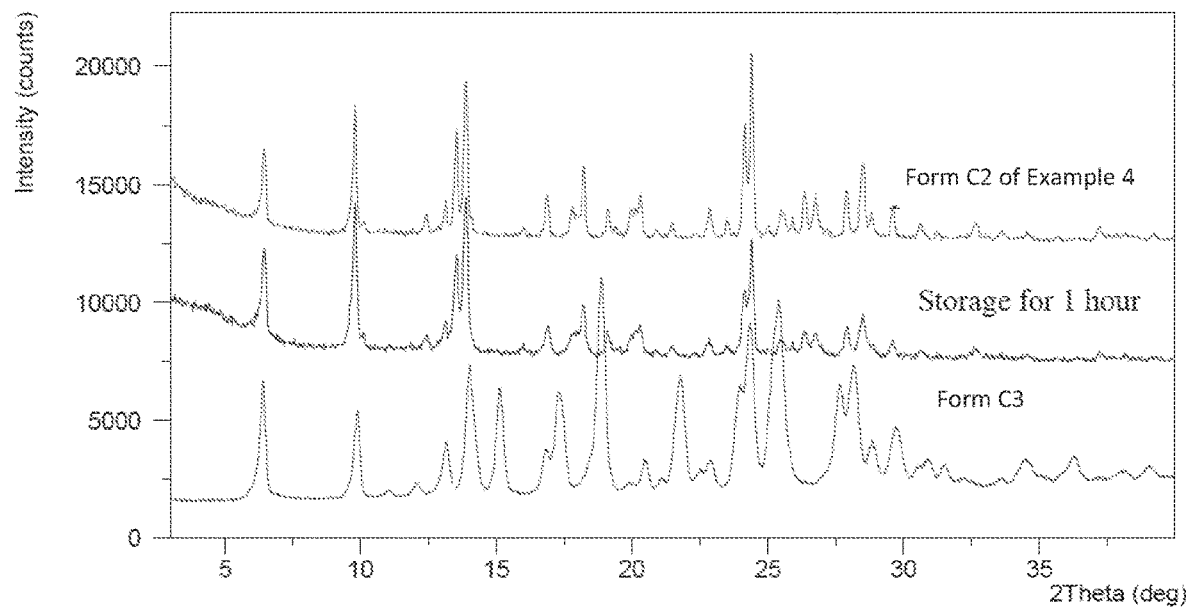
FIG. 6D shows XRPD patterns overlay of Form C3 before and after storage (in Example 5).
Figure 7A:
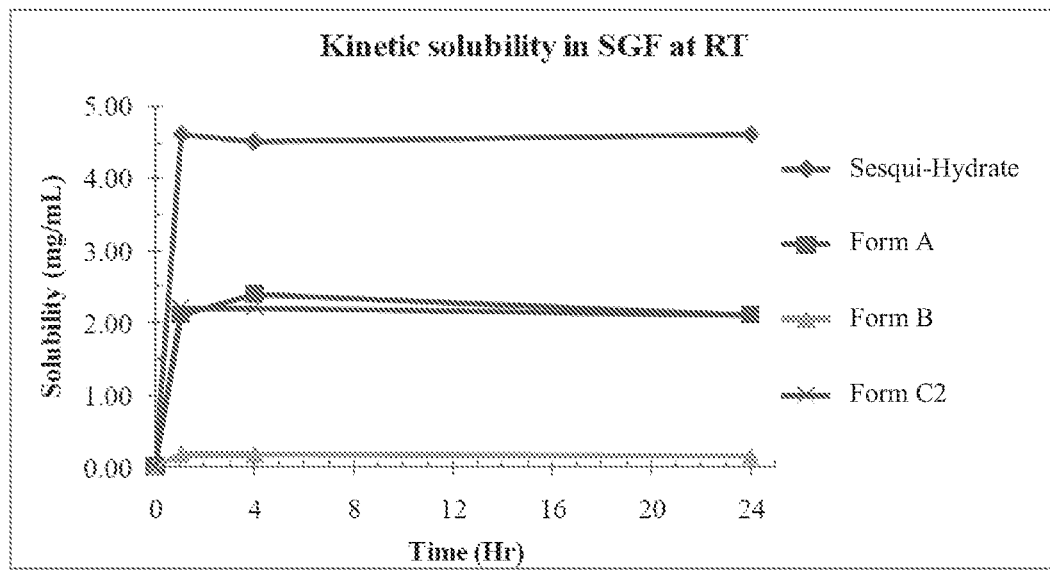
FIGS. 7A-7D show Kinetic solubility profiles of Form A, Form B, Form C2 at room temperature (25±3° C.).
Figure 7B:
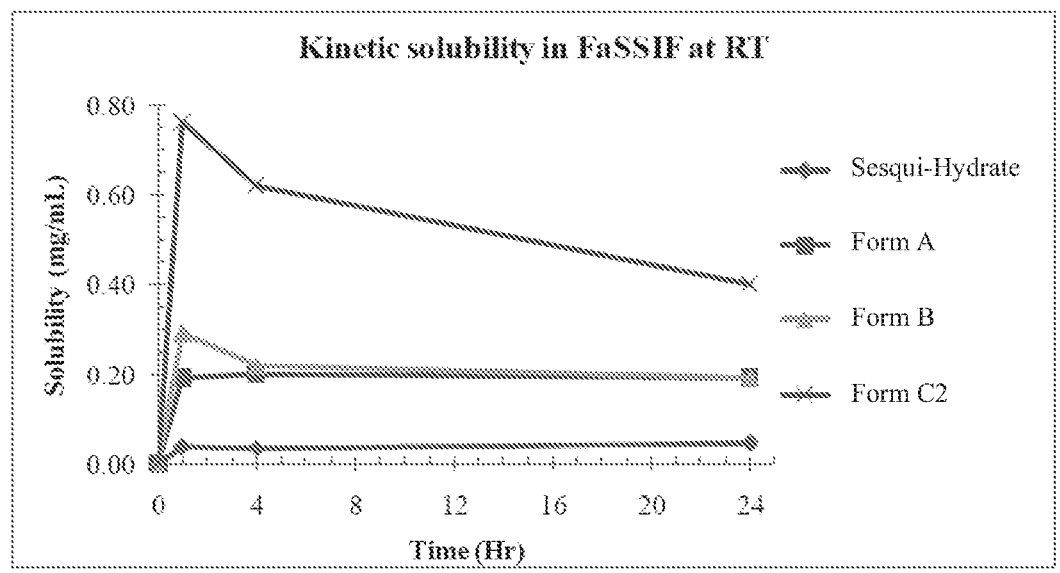
Figure 7C:
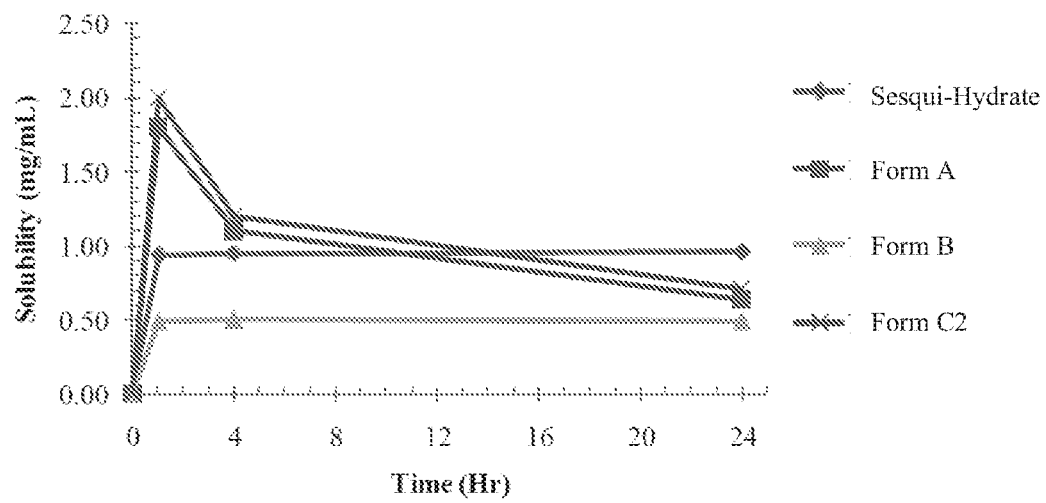
Figure 7D:
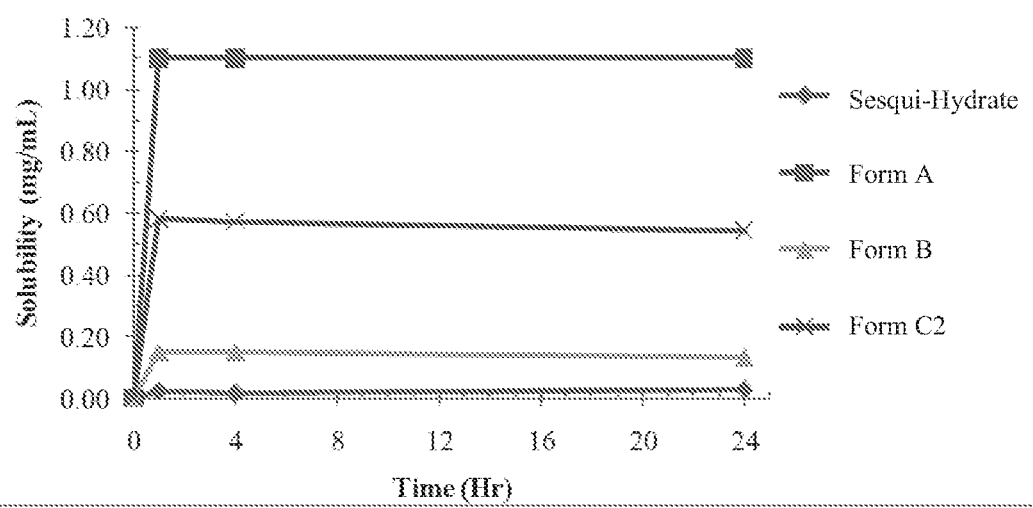

The XRPD pattern of the resultant solid was consistent with that of FIG. 5A, also named as Form C2. The TGA/DSC curves in FIG. 6A showed a two-step weight loss of 1.1% and 6.1% before 120° C. with a broad endotherm at 115.2° C. (onset temperature) followed by decomposition. The stoichiometry ratio (acid/freebase) of is Form C2 was 1.0 according to the result of NMR; see FIG. 6B.

To confirm the form change during heating of Form C2, VT-XRPD was conducted under protection of nitrogen. As the results showed, a new form named as Form C3 was observed after heating Form C2 to 140° C. and cooling back to 30° C. with $N_2$ flow (see FIG. 6C and it converted back to Form C2 after exposure to ambient conditions (~25° C./70% RH) within 1 hour (see FIG. 6D). Associated with the results of VT-XRPD, Form C2 was speculated to be a hydrate, theoretical water content for sesqui-hydrate is 6.1%, with good physical stability at ambient conditions.

Example 6: Physicochemical Properties Test

Forms A, B and C2 prepared herein were further studied for their solid-state stability, solubility/dissolution, and hygroscopicity.

I. Solid-State Stability Test

Each sample (Forms A, B or C2) was exposed to both conditions of 25° C./60% RH and 40° C./75% RH. After one-week storage, all the samples were characterized by XRPD to test any solid form change and by HPLC to check the purity change. As shown in Table 10, no solid form or HPLC purity change was observed for any salt, indicating good physical and chemical stability of the crystalline forms disclosed herein under tested conditions.

TABLE 10

Stability evaluation for one week

| Solid form | Initial purity (area %) | 25° C./60% RH (7 days) | | 40° C./75% RH (7 days) | |
| --- | --- | --- | --- | --- | --- |
| | | Purity of initial (%) | Form change | Purity of initial(%) | Form change |
| Form A | 99.5 | 100.1 | NO | 100.1 | NO |
| Form B | 99.4 | 100.2 | NO | 100.1 | NO |
| Form C2 | 99.5 | 100.2 | NO | 100.0 | NO |

II. Kinetic Solubility Test

About 20 mg of each sample (Forms A, B or C2) was equilibrated in 3.0 mL of three bio-relevant media, i.e., fasted state small intestinal fluid (FaSSIF), Fed State Simulating Intestinal Fluid (FeSSIF) and Simulated Gastric Fluid (SGF), or $H_2O$ into each 4-mL plastic vial. The suspensions were mixed via triturating (25 rpm) at RT, with each suspension sampled at the end of 1 hr, 4 hrs and 24 hrs, respectively. The kinetic solubility profiles of crystalline forms disclosed herein were showed in FIGS. 7A-7D.

Compared with Crystalline Sesqui-Hydrate of Compound 1, all the three salts showed improved solubility in water but smaller in SGF. Steady dissolution rate and comparable solubility was observed for Form B in FaSSIF (~0.2 mg/mL) and FeSSIF (~0.5 mg/mL), indicating a significantly decreased food-effect. On the other hand, the particular steady dissolution profile of Form B also suggests its potential use in an extended release formulation. The solid of Form B was physically stable even after suspended in the media for up to 24 hours. For Form A and Form C2, good solubility was observed in FaSSIF and FeSSIF at the first time point, but the values went down after equilibrated for a longer time, which might be caused by the solid form change.

III. Hygroscopicity Test

To investigate the solid form stability as a function of humidity, DVS isotherm plot (at 25° C.) and XRPD pattern were collected, see Table 11. The uptake percentage differences between desorption and adsorption are speculated to be related to the replacement of possible residual solvent with moisture.

TABLE 11

DVS results

| | Water uptake % at 80% RH | | | Form |
| --- | --- | --- | --- | --- |
| Solid form | Desorption | Adsorption | Hygroscopicity* | change |
| Form A | 2.1 | 1.9 | Hygroscopic | NO |
| Form B | 2.4 | 0.7 | Slightly hygroscopic | NO |
| Form C2 | 0.3 | 0.2 | Slightly hygroscopic | NO |

*concluded from the water uptake from adsorption cycle.

The efficacy of Compound 1 on BRCA1/2 mutant activities can be found in the unpublished PCT application PCT/CN2016/096200, the entire contents of which are incorporated herein by reference.

Test 1: Inhibition and Selectivity of poly(ADP-ribosyl)ation (PARylation) Enzymes by Crystalline Sesqui-Hydrate of Compound 1

Biochemical potency of Compound 1 Sesqui-Hydrate in inhibiting poly(ADP-ribosyl)ation (PARylation) activity of PARP1, PARP2, TNKS1 and TNKS2 was determined by using commercial PARP1/2 Chemiluminescent Assay Kits (BPS Bioscience Inc.) and. GST-tagged-enzymes were expressed and purified from baculovirus infected Sf9 cell (see Table 12 for enzyme constructs). PARP1 and PARP2 enzymes were from the assay kits, while TNKS1 and TNKS2 enzymes were produced in-house. The assays were performed according to the manufacture's instruction. Briefly, H2A and H2B proteins were immobilized on the surface of plates and then incubated with a serial dilution of compounds and the target enzyme for 0.5 hr. Then, biotinylated NAD and DNA (no DNA needed for TNKS1 or TNKS2) were added to the wells to initiate reactions. The biotinylated PARsylation product was measured by chemiluminescence after adding streptavidin-HRP and HRP substrates. The IC50s of Compound 1 sesqui-hydrate were derived from fitting the dose-response % inhibition data to the four-parameter logistic model using Graphpad Prism software.

Table 12 summarizes IC50s of Compound 1 sesqui-hydrate for PARP1, PARP2, TNKS1 and TNKS2 enzymes. As shown in Table 12 Compound 1 sesqui-hydrate potently inhibits catalytic activity of PARP1 and PARP2, with IC50 of 1.3 and 0.92 nM, respectively. It is more than 100-fold weaker in inhibition of TNKS1 and TNKS2 than PARP1 or PARP2.

TABLE 12

INHIBITION OF PARPS BY COMPOUND 1 SESQUI-HYDRATE IN BIOCHEMICAL ASSAYS

| Enzyme | $IC_{50}$ of Compound 1 sesqui-hydrate |
|---|---|
| Full length PARP1 | 1.3 ± 0.058 nM (n = 3) |
| PARP2 (aa2-583) | 0.92 nM |
| TNKS1 (aa1021-1327) | 0.23 μM |
| TNKS2 (aa667-1166) | 0.14 μM | n: number of determinations;
n = 1 where not specified.

Test 2: Intracellular Target Inhibition

HeLa cells were gifted from National Institute of Biological Sciences (Beijing) and maintained in DMEM supplemented with fetal bovine serum (10% FBS), 100 units/mL penicillin and 0.1 mg/mL streptomycin and kept at 95% humidity and 5% $CO_2$ in a 37° C. incubator. Upon incubation with hydrogen peroxide ($H_2O_2$), Intracellular PARP activity was induced and endogeous PAR level was elevated. The assay was performed as follows:

Cells were plated into a 96-well plate with clear bottom and black wall at a density of 5000 cells per well (100 μL). The plates were incubated for 4 hours at 37° C. under 5% CO2 atmosphere, and then incubated with specific concentrations of test compounds (typically 0.01 nM-10 μM). In the following day, $H_2O_2$ solution in PBS (final concentration 200 μM) was added and the plate was kept at 37° C. for 5 minutes. Then the medium was gently removed by plate inversion, and the cells were fixed by ice-cold MeOH at −20° C. for 20 minutes. After removal of the fixative and repeated wash with PBS, the detection buffer (50 μL/well, containing PBS, Tween (0.1%), and BSA (1 mg/mL)) together with the primary PAR mAb (Alexis ALX-804-220, 1:2000), the secondary anti-mouse Alexa Fluor 488 antibody (Molecular Probes A11029, 1:2000), and nuclear dye DAPI (Molecular Probes D3571, 150 nM) were added and incubation at 4° C. in the dark overnight. After removal of solution and repeated wash with PBS, the PAR polymer level was estimated by ArrayScan VTI (ThermoFisher). Percent inhibition was determined on the basis of the residual enzyme activity in the presence of increasing PARP inhibitor concentration. $IC_{50}$ values were calculated by fitting dose-dependent data to the four-parameter logistic model using XLfit software.

Under these conditions, Crystalline Sesqui-Hydrate of Compound 1 inhibited intracellular PAR formation with an $IC_{50}$ of 0.24 nM and was more potent than veliparib and olaparib, which had cellular PAR formation $IC_{50}$s of 2.66 nM and 0.47 nM, respectively.

TABLE 13

INHIBITION OF CELLULAR PAR FORMATION IN HYDROGEN PEROXIDE PRE-TREATED HELA CELLS.

| | $IC_{50}$ (nM) in PARylation assay |
|---|---|
| Olaparib | 0.47 ± 0.13 (n = 10) |
| Veliparib | 2.66 ± 0.66 (n = 10) |
| Compound 1 sesqui-hydrate | 0.24 ± 0.10 (n = 10) |

Test 3: Synthetic Lethality of Cancer Cells Killing

MDA-MB-231 cells that is not BRCA gene mutant or other homologous recombination deficient were maintained in DMEM supplemented with fetal bovine serum (10% FBS), 100 units/ml penicillin and 0.1 mg/ml streptomycin. BRCA1-deficient cell line MDA-MB-436 was maintained in RPMI-1640 supplemented with 10% FBS, 100 units/ml penicillin and 0.1 mg/ml streptomycin. Both two cell lines were kept at 95% humidity and 5% $CO_2$ in a 37° C. incubator.

The number of tumor cells seeded per well of a 96-well plate was optimized for each cell line to ensure logarithmic growth over the 7 days treatment period. Cells were left to attach for 16 hours and then treated with specific concentrations of test compounds. Following a 7-day exposure to the compound, the growth-inhibitory activity of compounds was determined using CellTiter-Glo luminescent cell viability assay (Promega). Luminescent signal was measured using PHERAstar FS reader (BMG Labtech). Cell viability was expressed as relative to mock treatment control. EC50 values for growth inhibition were calculated by fitting dose-dependent data to the four-parameter logistic model using XLfit software.

Under these conditions, MDA-MB-231 of which BRCA gene is wildtype was relatively resistant to Compound 1 with $EC_{50}$s about 9 uM. In contrast, tumor cell lines that was BRCA1-deficient (MDA-MB-436) was profoundly sensitive to Compound 1. Compound 1 was shown to be more potent than veliparib and similar to olaparib in the tumor cells tested.

TABLE 17

SELECTIVE KILLING OF TUMOR CELLS WITH BRCA1 OR BRCA2 MUTATIONS

| Cell Line | Olaparib | Veliparib | Compound 1 |
|---|---|---|---|
| MDA-MB-231 | ~5000 | >10000 | ~9000 |
| MDA-MB-436 (BRCA1 Deficient) | 21 ± 7 | 820 ± 300 | 41 ± 15 |

Test 5: In Vivo Pharmacology of Crystalline Sesqui-Hydrate of Compound 1

The in Vivo pharmacodynamics activity (PD) of Compound 1 on PARP was evaluated in BALB/c nude mice bearing subcutaneous human MDA-MB-436 (BRCA1 mutant) breast cancer. In addition, the relationship between Compound 1 concentration (PK, pharmacokinetics) in plasma and tumor tissues and its effect on PARylation (PD, pharmacodynamics) was investigated in this xenograft model. Oral administration of Compound 1 resulted in time-dependent and dose-dependent inhibition of PARylation in MDA-MB-436 breast cancer xenografts in mice. Inhibition of PARylation in the tumor tissues correlates well with tumor drug concentrations of Compound 1. Potent inhibition of PARylation was observed at 4 hours after single oral dose of Compound 1 at 0.34 mg/kg or higher. At 5.45 mg/kg, Compound 1 induced a strong and sustained PARylation inhibition in MDA-MB-436 tumor tissues. Compound 1 induced a dose-dependent inhibition on PAR levels in MDA-MB-436 xenograft at 4 hours after single oral administration of 0.17 to 10.9 mg/kg of Compound 1. At 5.45 mg/kg, Compound 1 induced rapid and potent inhibition on PAR levels. The PARylation inhibition was 98% at 0.5 hour after treatment. This inhibition remained at a high level (>80%) through the first 12 hours but was back to 53% at 24 hours. These data support BID dosing in efficacy studies in mouse xenograft models. Both dose titration and time course study suggested that Compound 1 concentration in tumor tissues needs to be over 0.5 μmol/kg to achieve at least 80% PARylation inhibition.

The in vivo efficacy of Compound 1 was explored in H209 SCLC xenograft model to evaluate the combination effect of Compound 1 and Temozolomide (TMZ), a DNA alkylating agent. TMZ single agent was quite effective in this model. One cycle of treatment resulted in all animals tumor-free. However, resistance occurred quickly during the second cycle. Combination of Compound 1 and TMZ significantly delayed resistance without additional toxicity. Tumors remained sensitive to the combination treatment after multiple cycles. In order to investigate whether Compound 1 could overcome the TMZ resistance, TMZ-resistant (TR) H209 tumors were generated by treating the H209 tumors with multiple cycles of TMZ in vivo. The derived H209-TR lines remained sensitive to the combination of Compound 1 and TMZ in this xenograft mouse model. Compound 1 has significant brain penetration, making it attractive for combining with TMZ in treating brain tumors or tumors with brain metastasis. Mice with established intracranial H209 xenografts were used to further investigate the combination activity of Compound 1 and TMZ on SCLC in brain. Addition of Compound 1 significantly prolonged animal survival compared to TMZ single agent in this intracranial model.

Test 6: Toxicology of Crystalline Sesqui-Hydrate of Compound 1

The nonclinical toxicity profile of Compound 1 was characterized in both rats and dogs in single and repeat dose studies up to 28 days. The adverse effects included decrease in body weights or body weight gain and food consumption; decrease in WBC, NEUT, LYMP, RBC, HGB, HCT and APTT; and increase in PLT. The bone marrow was considered to be the major target organ and the severity of histopathological changes ranged from minimal to marked. The toxicity was dose dependent, correlated with systemic exposure and reversible after 28-day recovery phase. Compound 1 showed no apparent impact on hERG current with $IC_{50}$=25.97 μM. No mutagenicity was noted in an Ames assay. In summary, the available toxicological data are adequate to support the clinical development of Compound 1 on late stage and advanced cancer patients in phase I study. The toxicity could be monitored and manageable clinically.

Test 7: Pharmacokinetics of Crystalline Sesqui-Hydrate of Compound 1

The species used for the pharmacokinetic studies were rat and dog. Compound 1 had good to excellent oral bioavailability (>40%) in both species. Elimination half-lives ranged from 3.1 to 5.0 hours in rats and 1.5 to 2.5 hours in dogs after oral administration. Clearance was moderate in both rats (8.67-15.2 mL/min/kg) and dogs (18.3-18.5 mL/min/kg). Steady state volume of distribution in rats and dogs was 2.4 L/kg and 1.9 L/kg, respectively. There was no accumulation of Compound 1 following multiple oral dosing in both species.

Test 8: ADME of Crystalline Sesqui-Hydrate of Compound 1

Plasma protein binding (PPB) for Compound 1 was 95.7%, 88.9%, 79.0%, 84.9% and 85.0% in human, monkey, dog, rat, and mouse plasma, respectively. After oral administration in rats, Compound 1 was detected in all organs checked. The drug concentrations reached maximum at 0.25 to 1 hour post-dosing and decreased to less than 10% of the peak concentration at 24 hours post-dosing.

Compound 1 was metabolized slowly in human, dog, rat, and mouse liver microsomes, while quickly in monkey liver microsomes, with a total of 5 metabolites (M1, M2, M3, M4 and M5) identified. Six metabolites, M1, M2, M3, M5, M6 and M7, were observed in the feces, plasma, urine and bile of the rat after oral administration. Compound 1 was primarily excreted in feces. The accumulative excretion amounts of Compound 1 in feces were 15% to 20% (up to 48 hours) after oral administration. Less than 1% of Compound 1 was excreted in urine and bile in rats.

CYP3A was the major CYP isoform responsible for Compound 1 metabolism while CYP2C8 contribute to Compound 1 metabolism to a lesser extent. Compound 1 is a moderate inhibitor for CYP2C9 (IC50=6.48 μM) while its $IC_{50}$s for other CYP isozymes are all larger than 10 μM. Compound 1 is not an inducer of human CYP1A2, CYP2B6 and CYP3A.

Test 9: Clinical Trials

Using crystalline Sesqui-Hydrate of Compound 1 to prepare capsules, a Phase I clinical safety study was completed on 25 subjects administered bid doses of 2.5, 5, 10, 20, 40, 80 and 120 mg. The results showed that 2.5-120 mg bid doses were safe and well tolerated. Compound 1 treatment caused partial or complete responses in BRCA1/2 mutant ovary cancer patients. These preliminary data demonstrated that crystalline Sesqui-Hydrate of Compound 1 was effective in the treatment of BRCA1/2 mutant or HR-deficient cancers.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

The invention claimed is:

1. A crystalline form of a salt of Formula I,

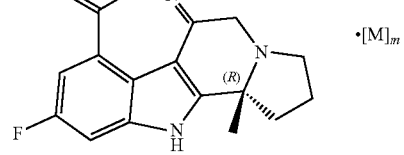

Formula I wherein M is selected from the group consisting of $H_3PO_4$, maleic acid and fumaric acid, and m is a number selected from a range between about 0.5 to about 2.0.

2. The crystalline form of claim 1, which is a phosphate salt of Formula Ia,

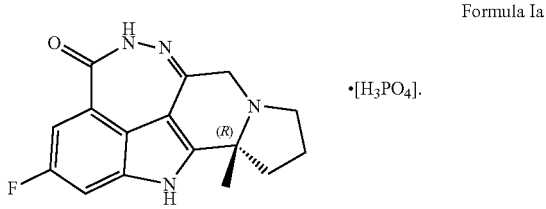

Formula Ia

3. The crystalline form of claim 2, wherein the crystalline form is a mono-hydrate.

4. The crystalline form of claim 3, wherein the crystalline form has:
  a) an X-ray powder diffraction pattern comprising diffraction peaks having 2θ angle values independently selected from the group consisting of: approximately 6.5±0.2°, 10.2±0.2°, and 25.2±0.2°;
  b) an X-ray powder diffraction pattern comprising diffraction peaks having 2θ angle values independently selected from the group consisting of: approximately 6.5±0.2°, 10.2±0.2°, 13.7±0.2°, 20.5±0.2°, and 25.2±0.2°;
  c) an X-ray powder diffraction pattern comprising diffraction peaks having 2θ angle values independently selected from the group consisting of: approximately 6.5±0.2°, 10.2±0.2°, 13.4±0.2°, 13.7±0.2°, 19.5±0.2°, 20.6±0.2°, 25.2±0.2°, and 27.6±0.2°; or
  d) an X-ray powder diffraction pattern comprising diffraction peaks having 2θ angle values independently selected from the group consisting of: approximately 6.5±0.2°, 10.2±0.2°, 12.9±0.2°, 13.4±0.2°, 13.7±0.2°, 18.9±0.2°, 19.5±0.2°, 20.6±0.2°, 25.2±0.2°, 26.9±0.2°, and 27.6±0.2°.

5. The crystalline form of claim 3, wherein the crystalline form has:
  a) an X-ray powder diffraction pattern substantially similar to FIG. 2A;
  b) a DSC thermogram substantially similar to FIG. 2B; and/or
  c) a TGA thermogram substantially similar to FIG. 2B.

6. The crystalline form of claim 1, which is a maleate salt of Formula Ib,

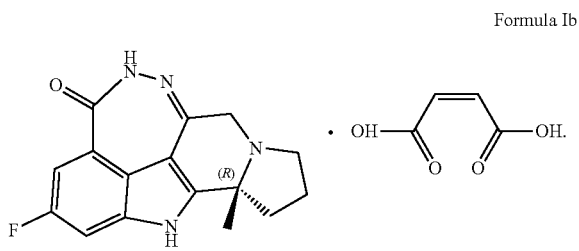

Formula Ib

7. The crystalline form of claim 6, wherein the crystalline form is an anhydrate.

8. The crystalline form of claim 7, wherein the crystalline form has:
  a) an X-ray powder diffraction pattern comprising diffraction peaks having 2θ angle values independently selected from the group consisting of: approximately 6.3±0.2°, 10.0±0.2°, 14.1±0.2°, and 25.0±0.2°;
  b) an X-ray powder diffraction pattern comprising diffraction peaks having 2θ angle values independently selected from the group consisting of: approximately 6.3±0.2°, 10.0±0.2°, 14.1±0.2°, 17.8±0.2°, 19.2±0.2°, and 25.0±0.2°;
  c) an X-ray powder diffraction pattern comprising diffraction peaks having 2θ angle values independently selected from the group consisting of: approximately 6.3±0.2°, 10.0±0.2°, 12.8±0.2°, 14.1±0.2°, 17.3±0.2°, 17.8±0.2°, 19.2±0.2°, 19.5±0.2°, 25.0±0.2°, 26.1±0.2°, and 28.2±0.2°; or
  d) an X-ray powder diffraction pattern comprising diffraction peaks having 2θ angle values independently selected from the group consisting of: approximately 6.3±0.2°, 10.0±0.2°, 12.8±0.2°, 14.1±0.2°, 17.3±0.2°, 17.8±0.2°, 19.2±0.2°, 19.5±0.2°, 25.0±0.2°, 26.1±0.2°, 28.2±0.2°, and 29.3±0.2°.

9. The crystalline form of claim 7, wherein the crystalline form has:
  a) an X-ray powder diffraction pattern substantially similar to FIG. 3A;
  b) a DSC thermogram substantially similar to FIG. 3B; and/or
  c) a TGA thermogram substantially similar to FIG. 3B.

10. The crystalline form of claim 1, which is a fumarate salt of Formula Ic,

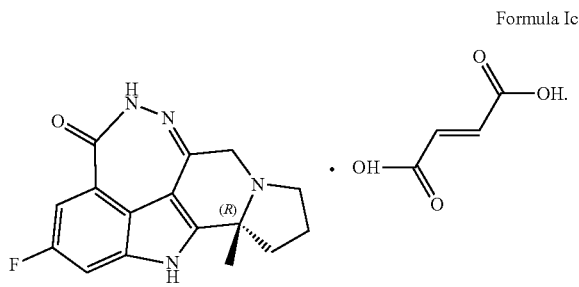

Formula Ic

11. The crystalline form of claim 10, wherein the crystalline form is a hydrate.

12. The crystalline form of claim 11, wherein the crystalline form is a sesqui-hydrate.

13. The crystalline form of claim 12, wherein the crystalline form has:
  a) an X-ray powder diffraction pattern comprising diffraction peaks having 2θ angle values independently selected from the group consisting of: approximately 6.4±0.2°, 9.8±0.2°, 13.8±0.2°, and 24.3±0.2°;
  b) an X-ray powder diffraction pattern comprising diffraction peaks having 2θ angle values independently selected from the group consisting of: approximately 6.4±0.2°, 9.8±0.2°, 13.4±0.2°, 13.8±0.2°, and 24.3±0.2°;
  c) an X-ray powder diffraction pattern comprising diffraction peaks having 2θ angle values independently selected from the group consisting of: approximately 6.4±0.2°, 9.8±0.2°, 13.4±0.2°, 13.8±0.2°, 18.2±0.2°, 24.0±0.2°, 24.3±0.2°, and 28.4±0.2°;

d) an X-ray powder diffraction pattern comprising diffraction peaks having 2θ angle values independently selected from the group consisting of: approximately 6.4±0.2°, 9.8±0.2°, 13.4±0.2°, 13.8±0.2°, 18.2±0.2°, 24.0±0.2°, 24.3±0.2°, 27.8±0.2°, and 28.4±0.2° e) an X-ray powder diffraction pattern comprising diffraction peaks having 2θ angle values independently selected from the group consisting of: approximately 6.4±0.2°, 9.8±0.2°, 13.4±0.2°, 13.8±0.2°, 18.2±0.2°, 20.2±0.2°, 24.0±0.2°, 24.3±0.2°, 27.8±0.2°, and 28.4±0.2°;

f) an X-ray powder diffraction pattern comprising diffraction peaks having 2θ angle values independently selected from the group consisting of: approximately 6.4±0.2°, 9.8±0.2°, 13.4±0.2°, 13.8±0.2°, 18.2±0.2°, 19.12±0.2°, 20.2±0.2°, 24.0±0.2°, 24.3±0.2°, 27.8±0.2°, and 28.4±0.2°;

g) an X-ray powder diffraction pattern comprising diffraction peaks having 2θ angle values independently selected from the group consisting of: approximately 6.4±0.2°, 9.8±0.2°, 13.1±0.2°, 13.4±0.2°, 13.8±0.2°, 16.8±0.2°, 18.2±0.2°, 19.12±0.2°, 20.2±0.2°, 22.8±0.2°, 24.0±0.2°, 24.3±0.2°, 26.3±0.2°, 27.8±0.2°, and 28.4±0.2°; or h) an X-ray powder diffraction pattern comprising diffraction peaks having 2θ angle values independently selected from the group consisting of: approximately 6.4±0.2°, 9.8±0.2°, 13.1±0.2°, 13.4±0.2°, 13.8±0.2°, 16.8±0.2°, 17.7±0.2°, 18.2±0.2°, 19.12±0.2°, 20.2±0.2°, 22.8±0.2°, 24.0±0.2°, 24.3±0.2°, 26.3±0.2°, 26.7±0.2°, 27.8±0.2°, 28.4±0.2°, and 29.5±0.2°.

14. The crystalline form of claim 13, wherein the crystalline form has:

a) an X-ray powder diffraction pattern substantially similar to FIG. 5A;

b) a DSC thermogram substantially similar to FIG. 5B; and/or c) a TGA thermogram substantially similar to FIG. 5B.

15. The crystalline form of claim 1, wherein the crystalline form is characterized by a purity of >85% or a purity of >95% or a purity of >99%.

16. A method of preparing a crystalline form of claim 1, comprising slurrying a suspension of a crystalline sesqui-hydrate of Compound 1 and an acid or anhydride thereof in a solvent at room temperature (25±3° C.) for 1 hour to 3 days or longer to obtain the crystalline form; wherein the acid is selected from the group consisting of $H_3PO_4$, maleic acid, and fumaric acid.

17. The method of claim 16, wherein the molar ratio of the crystalline sesqui-hydrate of Compound 1 and the acid is about 1.

18. The method of claim 16, wherein the solvent is ethyl acetate, acetone, acetonitrile, isopropanol/$H_2O$ (19:1, v:v) or a mixture thereof.

19. The method of claim 16, wherein the solvent is selected from the group consisting of acetone, acetonitrile, and isopropanol/$H_2O$ (19:1, v:v); and the crystalline form is:

a) a phosphate salt of Formula Ia:

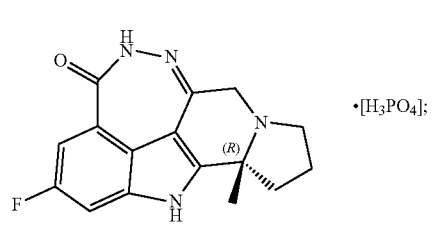

(Formula Ia)

or b) a maleate salt of Formula Ib,

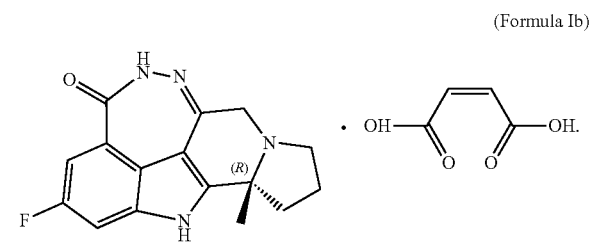

(Formula Ib)

20. The method of claim 16, wherein the solvent is isopropanol/$H_2O$ (19:1, v:v) and the crystalline form is a fumarate salt of Formula Ic,

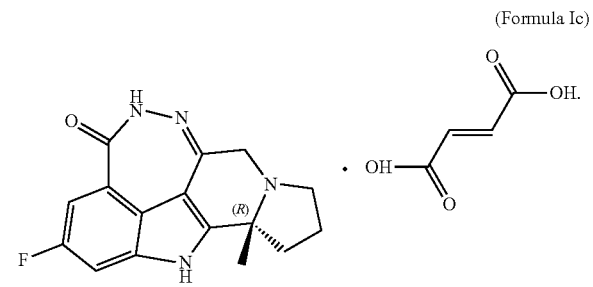

(Formula Ic)

21. The method of claim 16 further comprising: adding a seed crystal of the crystalline form into the suspension before or during slurrying.

22. The method of claim 16, wherein the suspension is formed by adding the solvent into the mixture of the crystalline sesqui-hydrate of Compound 1 and the acid or anhydride thereof.

23. A pharmaceutical composition comprising a therapeutically effective amount of the crystalline form of claim 1, and a pharmaceutically acceptable excipient.

24. A method of treating cancer associated with BRCA1/2 mutant activities in a subject in need thereof, comprising administering to the subject a therapeutically effective amount of the crystalline form of claim 1.

25. The crystalline form of claim 1, wherein m is a number of about 1.0.

26. The method of claim 16, wherein the duration of time for slurrying is about 1 day to 3 days.

* * * * *